(12) United States Patent
Kuutti et al.

(10) Patent No.: US 11,904,177 B2
(45) Date of Patent: Feb. 20, 2024

(54) POCKET-SIZED AUTOMATED EXTERNAL DEFIBRILLATOR

(71) Applicant: USA Medical Electronix, Inc., Norcross, GA (US)

(72) Inventors: Tommi Kuutti, Norcross, GA (US); Victor Tikhonov, Norcross, GA (US)

(73) Assignee: USA Medical Electronix, Inc., Norcross, GA (US)

( * ) Notice: Subject to any disclaimer, the term of this patent is extended or adjusted under 35 U.S.C. 154(b) by 0 days.

(21) Appl. No.: 18/032,926

(22) PCT Filed: Jan. 28, 2022

(86) PCT No.: PCT/US2022/014318
§ 371 (c)(1),
(2) Date: Apr. 20, 2023

(87) PCT Pub. No.: WO2022/165179
PCT Pub. Date: Aug. 4, 2022

(65) Prior Publication Data
US 2024/0017080 A1    Jan. 18, 2024

Related U.S. Application Data

(60) Provisional application No. 63/142,910, filed on Jan. 28, 2021.

(51) Int. Cl.
*A61N 1/39*    (2006.01)

(52) U.S. Cl.
CPC ......... *A61N 1/3904* (2017.08); *A61N 1/3912* (2013.01); *A61N 1/3968* (2013.01); *A61N 1/3981* (2013.01); *A61N 1/3987* (2013.01)

(58) Field of Classification Search
CPC .. A61N 1/3904; A61N 1/3912; A61N 1/3968; A61N 1/3981; A61N 1/3987
See application file for complete search history.

(56) References Cited

U.S. PATENT DOCUMENTS

| | | |
|---|---|---|
| 3,614,954 A | 10/1971 | Mirowski et al. |
| 3,703,900 A | 11/1972 | Holznagel |
| 3,716,059 A | 2/1973 | Welborn et al. |

(Continued)

*Primary Examiner* — Eric D. Bertram
(74) *Attorney, Agent, or Firm* — Eversheds Sutherland (US) LLP

(57) ABSTRACT

Automated External Defibrillator (AED) devices may include a high voltage capacitor (HV Cap) configured to store energy required to deliver a defibrillation shock to a patient; batteries configured to charge the HV Cap; a DC/DC converter circuit including a high voltage transformer, a FET switch with associated driver, and a rectifying diode; an H-bridge circuit configured to transform energy released from the HV Cap into a bi-phasic pulse; and a memory and microprocessor configured to operate the AED device. In particular, the HV Cap, the DC/DC converter circuit, the H-bridge circuit, the one or more batteries, and the memory and the microprocessor may contained in a pocket-sized housing, the AED device may be configured to continuously monitor and adjust the rate at which the batteries charge the HV Cap, and the AED device may include a variable frequency relaxation oscillator circuit configured to acquire a patients Z-body measurement.

20 Claims, 17 Drawing Sheets

(56) References Cited

U.S. PATENT DOCUMENTS

| | | | |
|---|---|---|---|
| 3,805,795 A | 4/1974 | Denniston et al. | |
| RE30,372 E | 8/1980 | Mirowski et al. | |
| RE30,387 E | 8/1980 | Denniston, III et al. | |
| RE30,750 E | 9/1981 | Diack et al. | |
| 5,107,834 A | 4/1992 | Ideker et al. | |
| 5,163,427 A | 11/1992 | Keimel | |
| 5,391,186 A | 2/1995 | Kroll et al. | |
| 5,405,361 A | 4/1995 | Persson | |
| 5,411,525 A | 5/1995 | Swanson et al. | |
| 5,474,574 A | 12/1995 | Payne et al. | |
| 5,800,460 A | 9/1998 | Powers et al. | |
| 5,908,443 A | 6/1999 | Brewer et al. | |
| 6,029,085 A | 2/2000 | Olson et al. | |
| 6,083,246 A | 7/2000 | Stendahl et al. | |
| 6,408,206 B1 | 6/2002 | Kroll et al. | |
| 6,417,649 B1 * | 7/2002 | Brink | A61N 1/3981 320/166 |
| 6,539,255 B1 | 3/2003 | Brewer et al. | |
| 6,662,046 B2 | 12/2003 | Hansen | |
| 6,778,860 B2 | 8/2004 | Ostroff et al. | |
| 6,865,417 B2 | 3/2005 | Rissmann et al. | |
| 6,871,093 B2 | 3/2005 | Hansen | |
| 6,952,608 B2 | 10/2005 | Ostroff | |
| 6,954,670 B2 | 10/2005 | Ostroff | |
| 6,963,773 B2 | 11/2005 | Waltman et al. | |
| 6,993,386 B2 | 1/2006 | Lin et al. | |
| 7,072,712 B2 | 7/2006 | Kroll et al. | |
| 7,236,823 B2 | 6/2007 | Herbert | |
| 7,277,753 B2 | 10/2007 | Mills et al. | |
| 7,555,339 B2 | 6/2009 | Nielsen et al. | |
| 7,623,920 B2 | 11/2009 | Ostroff | |
| 7,797,043 B1 | 9/2010 | Dupelle et al. | |
| 7,865,238 B2 | 1/2011 | Brink | |
| 8,036,742 B2 | 10/2011 | Sullivan et al. | |
| 8,086,306 B2 | 12/2011 | Katzman et al. | |
| 8,086,312 B2 | 12/2011 | Nielsen et al. | |
| 8,086,320 B2 | 12/2011 | Saketkhou | |
| 8,209,007 B2 | 6/2012 | McIntyre | |
| 8,335,562 B2 | 12/2012 | Hansen et al. | |
| 8,344,899 B2 | 1/2013 | Sullivan et al. | |
| 8,615,295 B2 | 12/2013 | Savage et al. | |
| 8,965,501 B2 | 2/2015 | Sullivan | |
| 9,138,591 B2 | 9/2015 | Abbenhouse et al. | |
| 9,307,383 B1 | 4/2016 | Patrick | |
| 9,517,354 B2 | 12/2016 | Schwibner et al. | |
| 9,543,074 B2 | 1/2017 | Park et al. | |
| D782,682 S | 3/2017 | Jung et al. | |
| 9,636,513 B2 | 5/2017 | Kuo et al. | |
| 9,737,723 B2 | 8/2017 | Einy | |
| 9,757,580 B2 | 9/2017 | Park et al. | |
| 9,789,326 B2 | 10/2017 | Schwibner et al. | |
| 9,827,432 B2 | 11/2017 | Wu | |
| 9,827,433 B2 | 11/2017 | Wu | |
| 9,839,789 B2 | 12/2017 | Kozin et al. | |
| D811,598 S | 2/2018 | Baek et al. | |
| 9,889,311 B2 | 2/2018 | Horseman et al. | |
| 10,055,548 B2 | 8/2018 | Jorgenson et al. | |
| 10,112,054 B2 | 10/2018 | Beyer et al. | |
| 10,149,973 B2 | 12/2018 | Raymond et al. | |
| 10,224,749 B2 | 3/2019 | Lee et al. | |
| 10,238,881 B2 | 3/2019 | Axness | |
| 10,279,189 B2 | 5/2019 | Raymond et al. | |
| 2003/0167075 A1 | 9/2003 | Fincke | |
| 2022/0193431 A1* | 6/2022 | Chapman | A61N 1/3993 |

* cited by examiner

POCKET-SIZED AUTOMATED EXTERNAL DEFIBRILLATOR

CROSS-REFERENCE TO RELATED APPLICATIONS

This application claims priority to U.S. Provisional Patent Application No. 63/142,910 filed Jan. 28, 2021, which is incorporated herein by reference.

FIELD OF THE INVENTION

The present disclosure relates generally to the medical electronics field, and more particularly to a portable Automated External Defibrillator (AED).

BACKGROUND

According to the World Health Organization, an estimated 18 million people die from cardiovascular diseases (CVD) each year, making CVD the number one cause of death globally. Every year, approximately 800,000 Americans have a heart attack and, according to the American Heart Association (AHA), approximately 300,000 Americans die each year from Sudden Cardiac Arrest (SCA).

People with risk factors such as hypertension, diabetes, or hyperlipidemia, or those with heart disease, are at the highest risk of a heart attack or SCA. And each year, approximately 200,000 people who have had a previous heart attack suffer a repeat occurrence. Many second heart attacks result in death.

Further, 70% of heart attacks are out-of-hospital cardiac arrests (OHCA), and 90% of OHCA incidence result in death. During cardiac arrest, survival depends on the speed at which a life-saving shock can be delivered to the heart by a defibrillator, and every minute of delay reduces the chances of survival by 10%. However, in the United States the average length of time between a 911 call and the arrival of Emergency Medical Services (EMS) is about 8 minutes, or 14 minutes in rural areas. As a result, most heart attack deaths occur because defibrillation therapy is not administered quickly enough.

Unfortunately, even if the ambulance or paramedics reach the victim within 8 minutes, brain injury may have already occurred, because irreversible brain damage may result from more than 5 minutes of oxygen deprivation. So even in the event a patient survives the cardiac episode, they may be in a permanently impaired state and unable to enjoy a full life thereafter.

In order to save lives, defibrillation therapy must be moved into the homes of people with risk factors for heart disease. However, conventional AEDs are typically found only in public places, such as airports and gyms. These conventional AEDs are big, bulky, and complicated, and are considered somewhat intimidating by most people. Conventional AEDs also are often placed in wall-mounted cabinets with a sign indicating that an alarm will sound when the door is opened. In emergency situations, this may be counterproductive as it increases the apprehension and anxiety of a potential Good Samaritan and consequentially may discourage them from getting involved. Moreover, it is estimated that up to 20% of conventional AEDs are not functional at any given time, yet many of these AEDs do not indicate noticeably enough if and when maintenance is needed.

Therefore, it would be desirable to enable defibrillation therapy closer to the people with risk factors for heart disease. It also would be desirable to provide an AED device that is compact enough to be carried by a family member or caretaker of the heart disease patient, easy to use, ready to use when and where needed, and provides very noticeable alerts whenever service or maintenance is required.

BRIEF SUMMARY

In one aspect, an Automated External Defibrillator (AED) device is provided which includes a high voltage capacitor (HV Cap) configured to store the energy required to deliver a defibrillation shock to a patient; one or more batteries configured to charge the HV Cap; a DC/DC converter circuit comprising a high voltage transformer (HV XFMR), a field effect transistor (FET) switch with associated driver, and a rectifying diode, preferably configured to increase the battery voltage to about 2000 volts; an H-bridge circuit configured to transform energy released from the HV Cap into a bi-phasic pulse; and a memory and a microprocessor which are configured to store and execute computer-executable instructions for operation of the AED device, wherein the HV Cap, the DC/DC converter circuit, the H-bridge circuit, the one or more batteries, and the memory and the microprocessor are contained in a pocket-sized housing. In embodiments, the AED device further includes a pair of defibrillator pads and a cable for operably connecting the HV Cap to the pair of defibrillator pads, wherein the defibrillator pads also are pocket-sized.

In another aspect, an AED device is provided which is configured to continuously monitor and adjust the rate at which the one or more batteries charge the HV Cap. In a preferred embodiment, the AED device is configured to simultaneously monitor discharge current and temperature of the one or more batteries in order to charge the HV Cap at the maximum rate possible with available power from the one or more batteries, while not exceeding either a maximum temperature or a maximum discharge rate of the one or more batteries.

In still another aspect, an AED device is provided which includes a variable frequency relaxation oscillator circuit configured to acquire a patient's Z-body measurement, wherein the circuit is effective to self-oscillate at a frequency that is proportional to the patient's body impedance.

In yet another aspect, an AED device is provided which includes a power handler circuit comprising a real time clock (RTC) and does not enter a sleep mode when the main microprocessor is powered off, wherein the power handler circuit is configured to control the AED device when the main microprocessor is powered off by way of the RTC, which is configured to periodically turn on the main microprocessor to perform a built-in self-test (BIST) sequence.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale.

DETAILED DESCRIPTION

Figure 1A:
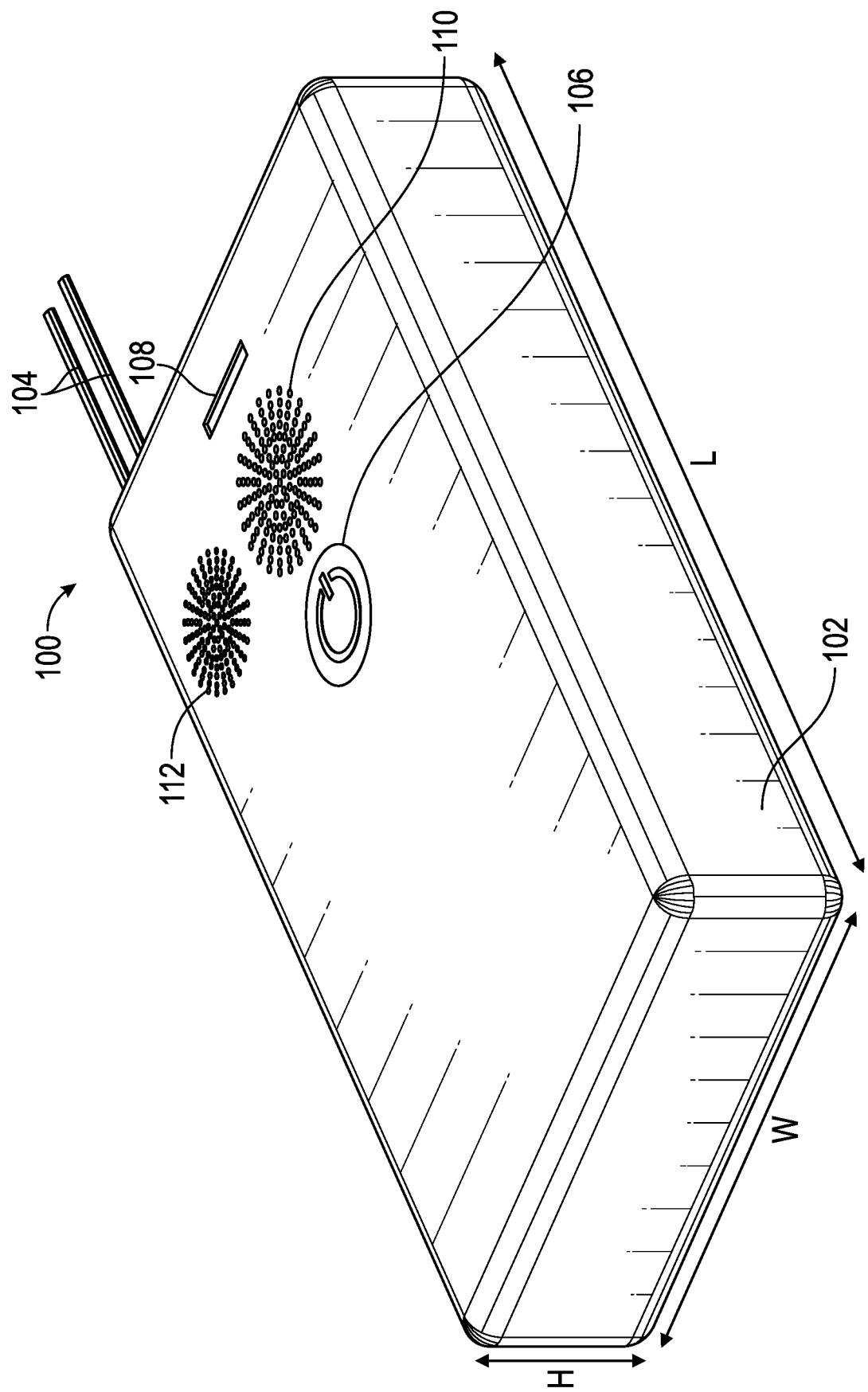
FIG. 1A is a front perspective view of an AED device, according to one embodiment of the disclosed invention.

A new, more compact Automated External Defibrillator (AED) device has been developed. It advantageously is pocket-sized, a size which is achieved by combining unique hardware and software components with the operational innovations described herein. Because the AED device is small enough to be carried with the patient, it advantageously can be present whenever and wherever it might be needed.

As used herein, the term "pocket sized" means that the AED device is small enough to be carried on a person in a jacket or pants pocket, or in a small purse or handbag, such as having dimensions less than or equal to 170 mm×95 mm×40 mm.

One of the keys to reducing the size and weight of the AED as compared to conventional AEDs is reduce the size and/or number of the batteries required by the device. This obviously reduces the amount of power stored and available to operate the AED device, and therefore necessitated several power saving and operational innovations, as described below, in order to meet regulatory performance requirements while maintaining or exceeding other performance expectations, such as reliability, maintenance/service intervals, and the like. In a preferred embodiment, the AED device as disclosed herein uses four CR2 batteries. While CR2 batteries are preferred because of the combination of size, charge time, and available power supply, the AED device can be adapted to use other suitable types or numbers of commercially available batteries that meet the size and performance requirements of the presently disclosed AED device.

Similarly, the dimensions of the defibrillator pads used in the present AED are also reduced as compared to the large sized defibrillator pads that are used in conventional AEDs. In a preferred embodiment, following the minimum allowable pad size according to the FDA, the pad size has been reduced to 6.0"×3.3" (152 mm×84 mm) with no loss of effectiveness, which is a reduction in size compared to those of conventional AEDs.

The AED device measures the patient's body impedance, calculates the energy required to deliver the appropriate shock, analyzes the patient's electrocardiogram (ECG), determines whether the patient has a shockable rhythm, and delivers the appropriate energy as a life-saving shock. Yet, advantageously, the AED device described herein is small enough that it may be easily carried by a heart disease patient or his or her family member or other caretaker, for example in a garment pocket, handbag, or backpack. Accordingly, the AED device facilitates saving lives by moving defibrillation therapy into the home and other places where conventional AEDs are absent and/or where timely access to emergency medical service personnel is unavailable.

In addition, the present AED device advantageously provides several features to facilitate its use and dependability. For example, in embodiments, the AED device includes a speaker that provides voice prompts that calmly guide the user on what to do during an emergency. In addition, the speaker also informs the user when the batteries or defibrillator pads need to be changed, when the internal temperature of the device is too hot, or when other service is required. The voice prompts can be programmed in many languages. Furthermore, in preferred embodiments, the AED device conducts a number of self-checks so that it is ready when needed or else will alert the user in the event of microprocessor, speaker or other failure, e.g., with the AED device's included LEDs and a piezo-buzzer, so that maintenance service can be conducted on the AED device before the AED device is sought to be used.

In preferred embodiments, the front face of the AED device is uncluttered with minimal buttons and text to distract or intimidate the user. For instance, in a preferred embodiment, the AED device includes only a single button for a user to "turn on" the device to initiate its use. In some other embodiments, the AED is activated by a capacitive switch that turns on the device whenever the user touches it or by a motion sensor that turns on the device whenever motion is detected (e.g., upon removal from a storage pouch, sleeve). In these embodiments, the goal is to make it as simple as possible for the user to use the device during a stressful medical situation.

Figure 1B:
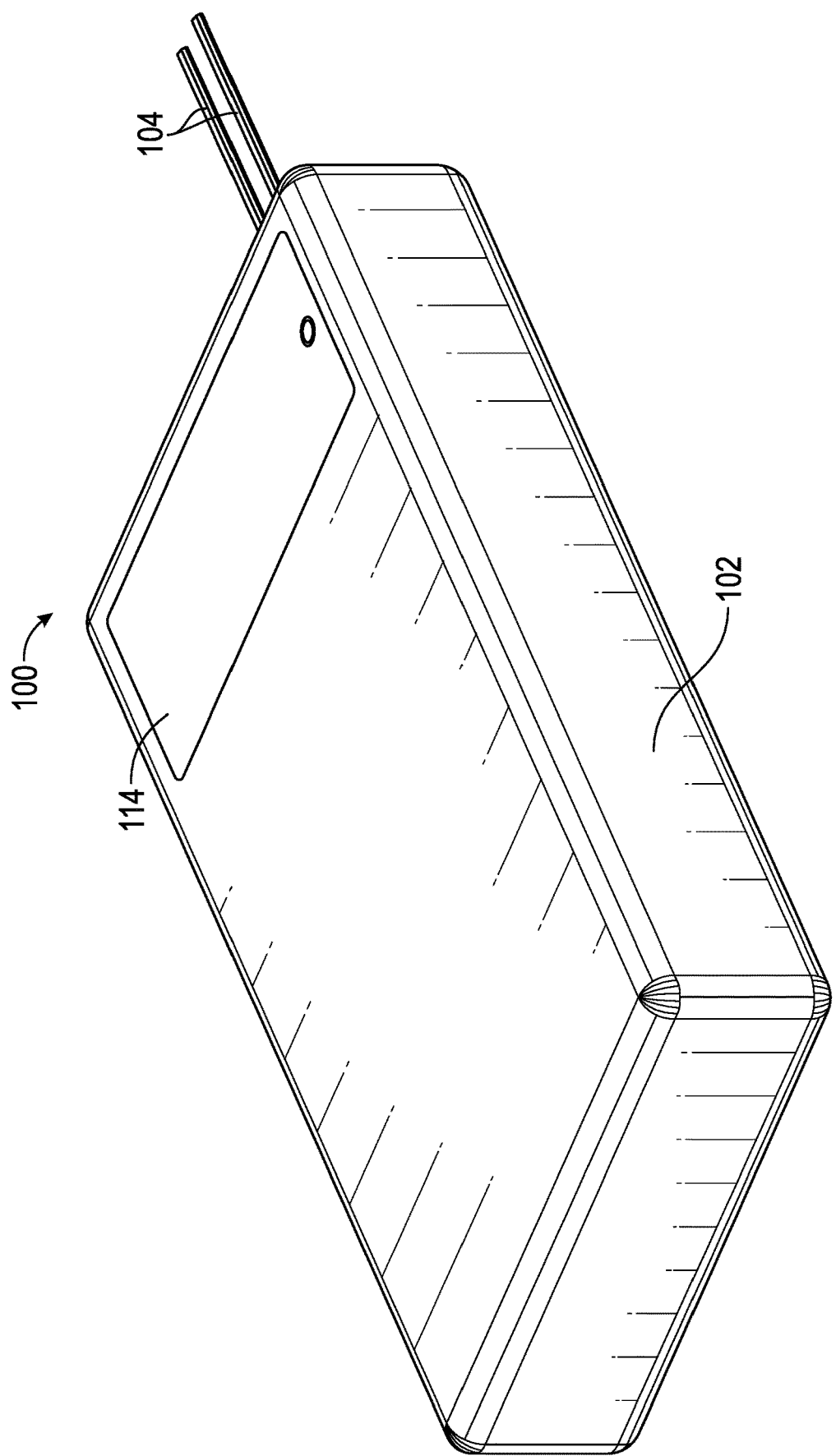
FIG. 1B is a back perspective view of the AED device shown in FIG. 1A.

A preferred embodiment of the AED device is shown in FIGS. 1A-1B. The AED device 100 includes a housing 102 which contains the internal electronic components of the device 100. In a preferred embodiment, the housing 102 measures 6.1 inches (155 mm) in length (L), 3.4 inches (86 mm) in width (W), and 1.1 inches (28 mm) in height (H) and weighs only about one pound (450 g).

As shown in FIG. 1A, the face of the housing 102 is uncluttered and includes a single ON button 106, speaker holes 110, piezo buzzer holes 112, and LED status lights 108. The AED device 100 does not include an OFF button, thereby preventing users or bystanders from inadvertently turning off the device during use. As shown in FIG. 1B, the back side of the housing 102 has a battery compartment cover 114, which is configured to provide access to batteries in the AED device 100. Extending from the top of the housing 102 are two defibrillator cables 104 (that connect to corresponding defibrillator pads 202, 204, which are shown in FIGS. 2A-2B).

When not in use, the AED device 100, defibrillator cables 104, and defibrillator pads 202, 204 may be stored together in a small pouch, sleeve, or case (not shown). For example, it may be soft fabric pouch, a bifold case, or the like. The pouch, sleeve, or case may be designed to minimize muffling or obscuring, respectively, audible or visual service notifications emitted by the AED device.

Figure 2A:
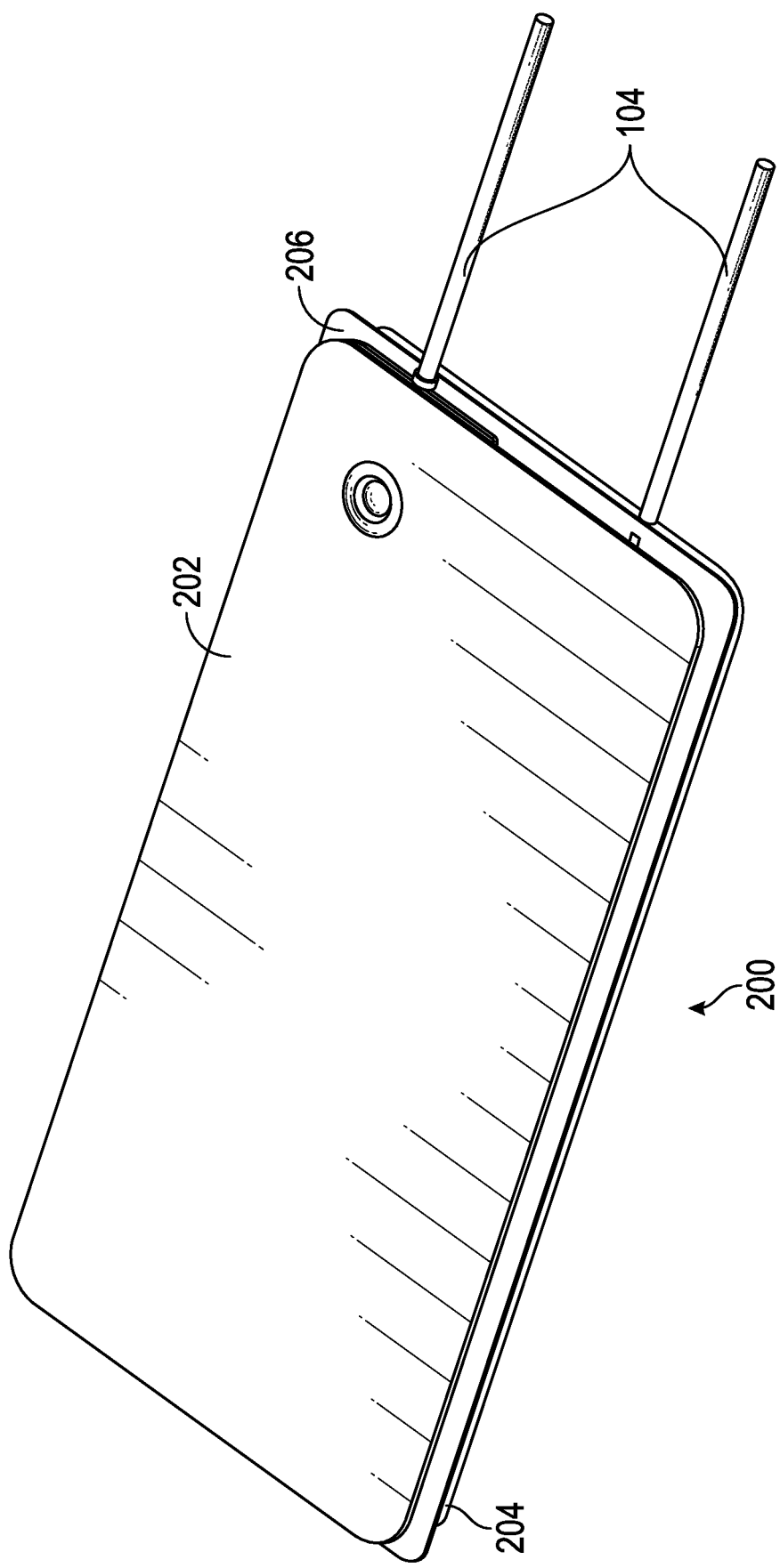
FIG. 2A is a perspective view of defibrillator pads arranged for packaging, according to one embodiment of the disclosed invention.
Figure 2B:
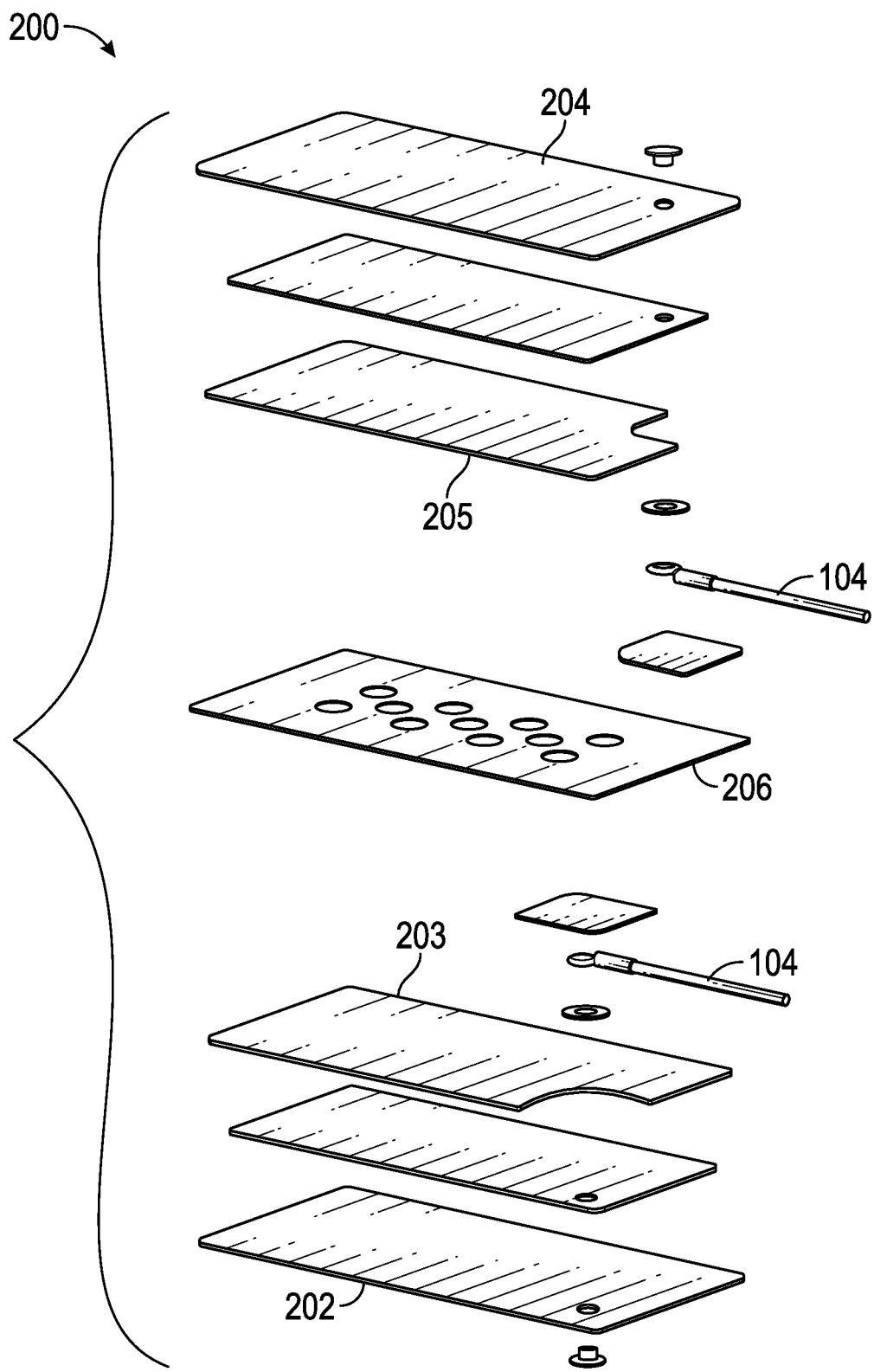
FIG. 2B is an exploded view of the defibrillator pads and components shown in FIG. 2A.

One embodiment of defibrillator pads 202, 204 is shown in FIGS. 2A-2B. The defibrillator pads 202, 204 are integrated with the defibrillator cables 104 such that, when the defibrillator pads 202, 204 are placed on the chest of the patient, the shock from the AED device travels through the defibrillator cables 104 to the defibrillator pads 202, 204 to shock the patient. As shown in FIG. 2A, the defibrillator pad storage assembly 200 include a laminated paper 206 placed between the conductive gel layers 203, 205 of the defibrillator pads 202, 204, which are stored face-to-face in a sealed, air-tight pouch (not shown). This packaging configuration serves to help preserve the integrity of the conductive gel layers 203, 205. As the figures indicate, the defibrillator pads 202, 204 have similar length and width dimensions to the housing 102, which facilitates their compact storage together. In one embodiment, the defibrillator pads 202, 204 are approximately 6 cm long and 3 cm wide. Other defibrillator pad dimensions are possible, so long as the defibrillator pads comply with the relevant regulatory requirements. For example, the U.S. Food and Drug Administration (FDA) requires that defibrillator pads have a contact surface area of at least 150 $cm^2$ total, or 75 $cm^2$ for each pad.

FIG. 2B shows the construction of the defibrillator pads 202, 204 and the arrangement for packaging. Each defibrillator pad 202, 204 has a conductive side that is coated in a conductive gel layer 203, 205. A removable, pressure sensitive laminated paper 206 is placed between the conductive gel layers 203, 205 of the defibrillator pads 202, 204.

Figure 3A:
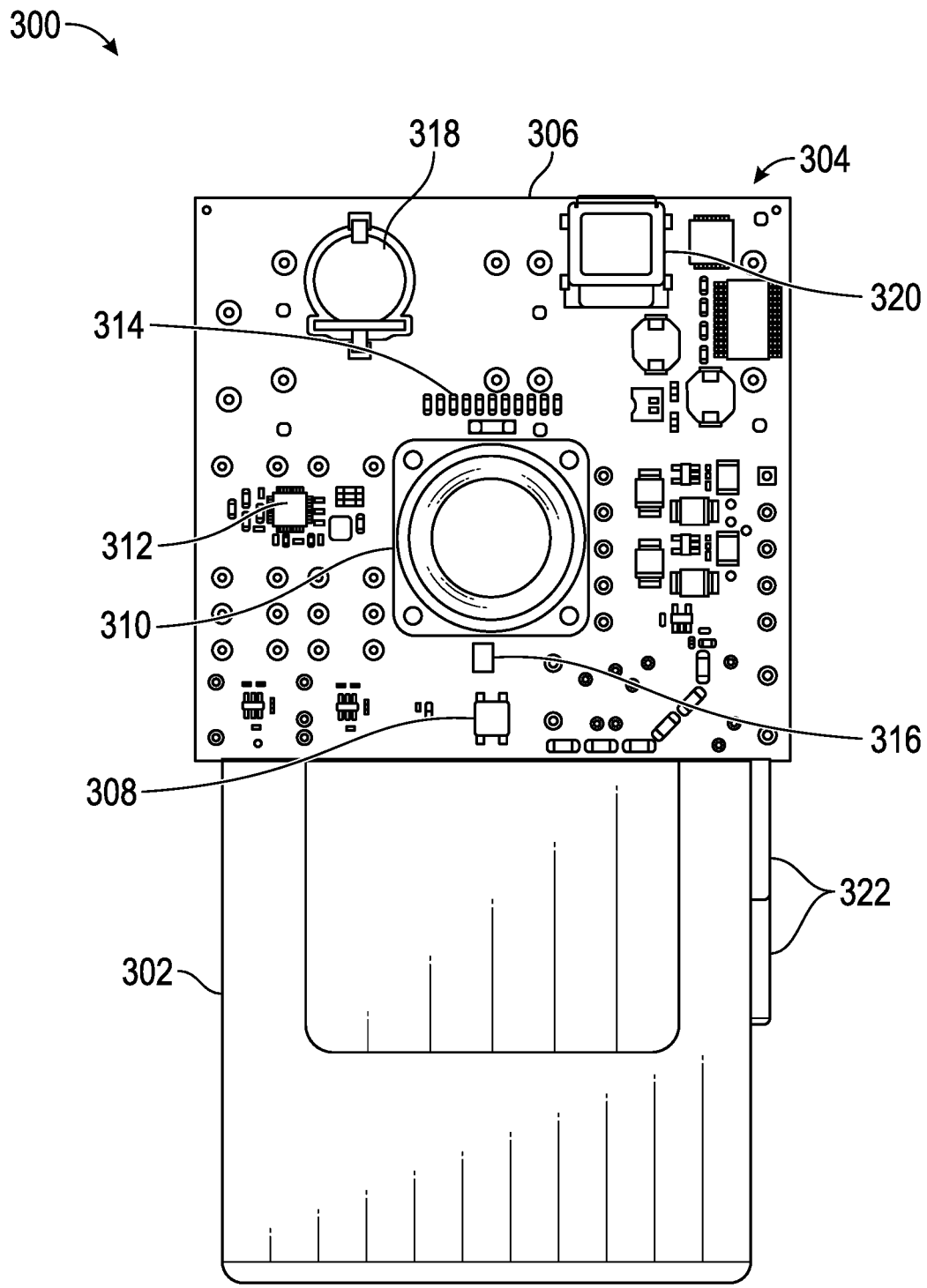
FIG. 3A is a front view of an AED circuit board and high voltage capacitor assembly, according to one embodiment of the disclosed invention.
Figure 3B:
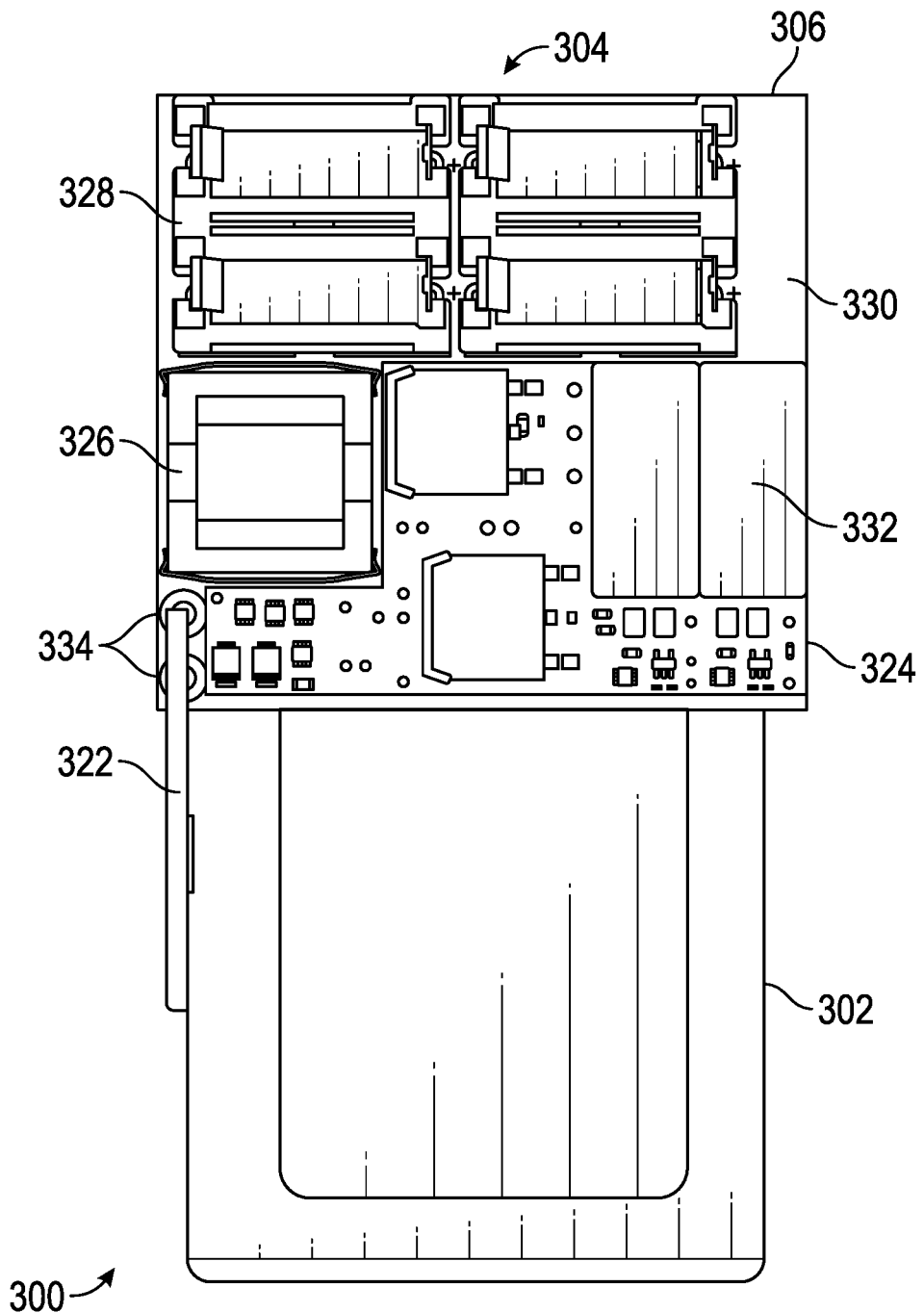
FIG. 3B is a back view of the AED circuit board and high voltage capacitor assembly shown in FIG. 3A.
Figure 4A:
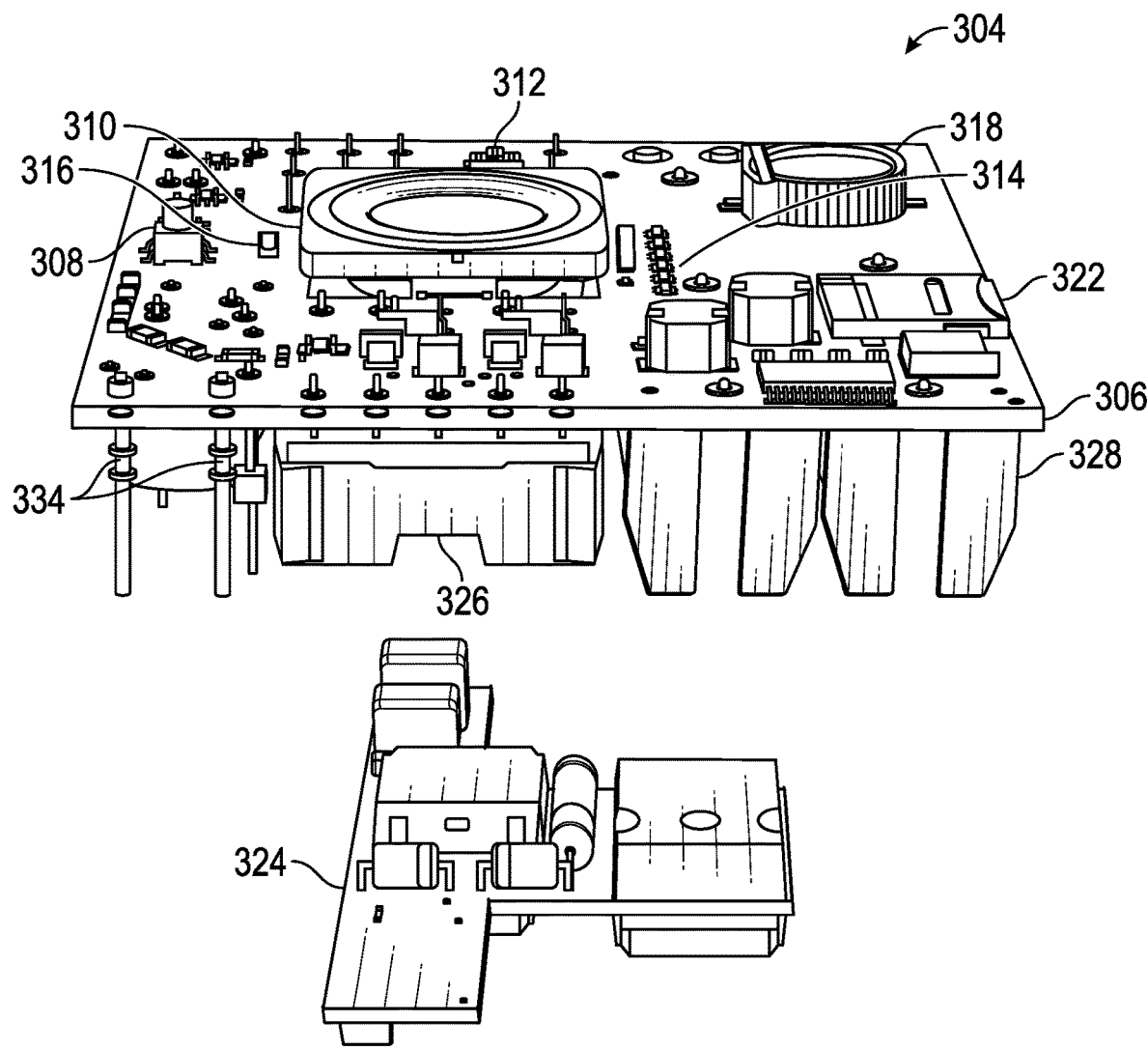
FIG. 4A is an exploded side view of an AED circuit board, according to one embodiment of the disclosed invention.
Figure 4B:
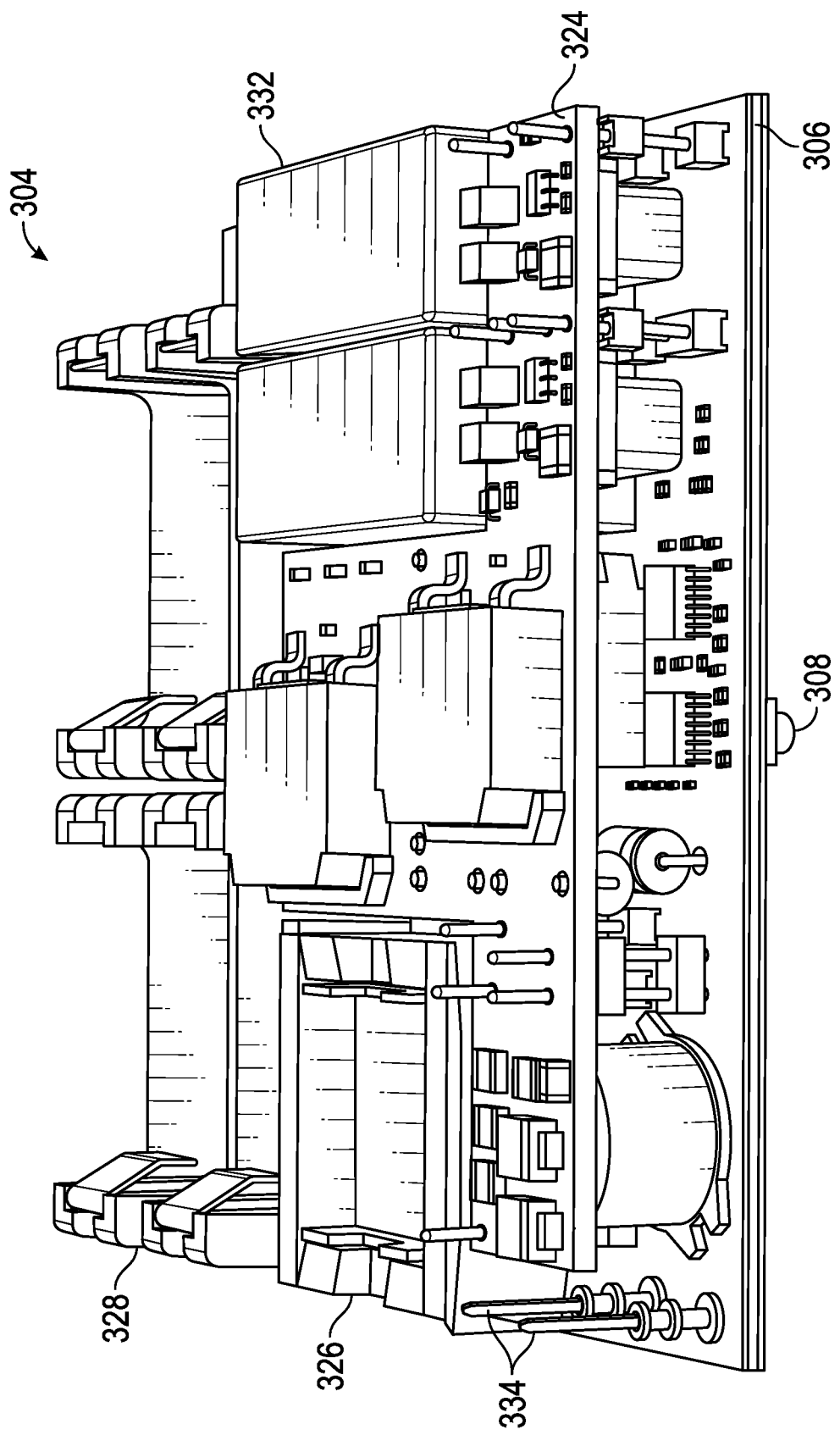
FIG. 4B is a back perspective view of the AED circuit board shown in FIG. 4A.

FIGS. 3A-3B show the internal electronic components of the AED device 100, including a high voltage capacitor (HV Cap) 302 and a circuit board 304 (depicted in greater detail in FIGS. 4A-4B), which together form the internal assembly 300. FIG. 3A depicts a front view of the internal assembly 300. According to this embodiment, electronic components are arranged on a main printed circuit board (PCB) 306. More specifically, the anterior side of the main PCB 306 holds the power button 308, speaker 310, piezo buzzer 312, LED status lights 314, a microphone 316, a backup battery 318, and a micro SD memory card 320. A primary microprocessor 602 and a secondary microprocessor (not shown) are also integrated into the main PCB 306. The HV Cap 302 is attached to the distal end of the circuit board 304 by capacitor leads 322, which connect to the capacitor contacts 334 located on the posterior side of the main PCB 306.

FIG. 3B depicts a back view of the internal assembly 300. The back side of the main PCB 306 holds four (4) battery compartments 328 sized to hold CR2 batteries (not shown), a high voltage transformer (HV XFMR) 326, capacitor contacts 334, and an area for defibrillator cable contacts 330. Thus, the HV Cap 302 is indirectly connected to the batteries (not shown) by way of the HV XFMR 326. In this embodiment, the HV XFMR 326 converts the power supplied by the batteries (not shown) to a level that can be received by the HV Cap 302. The back side of the main PCB 306 also includes relays 332 and an H-Bridge circuit on a secondary PCB 324, both of which, in various different configurations, are standard components of AED devices.

Figure 5:
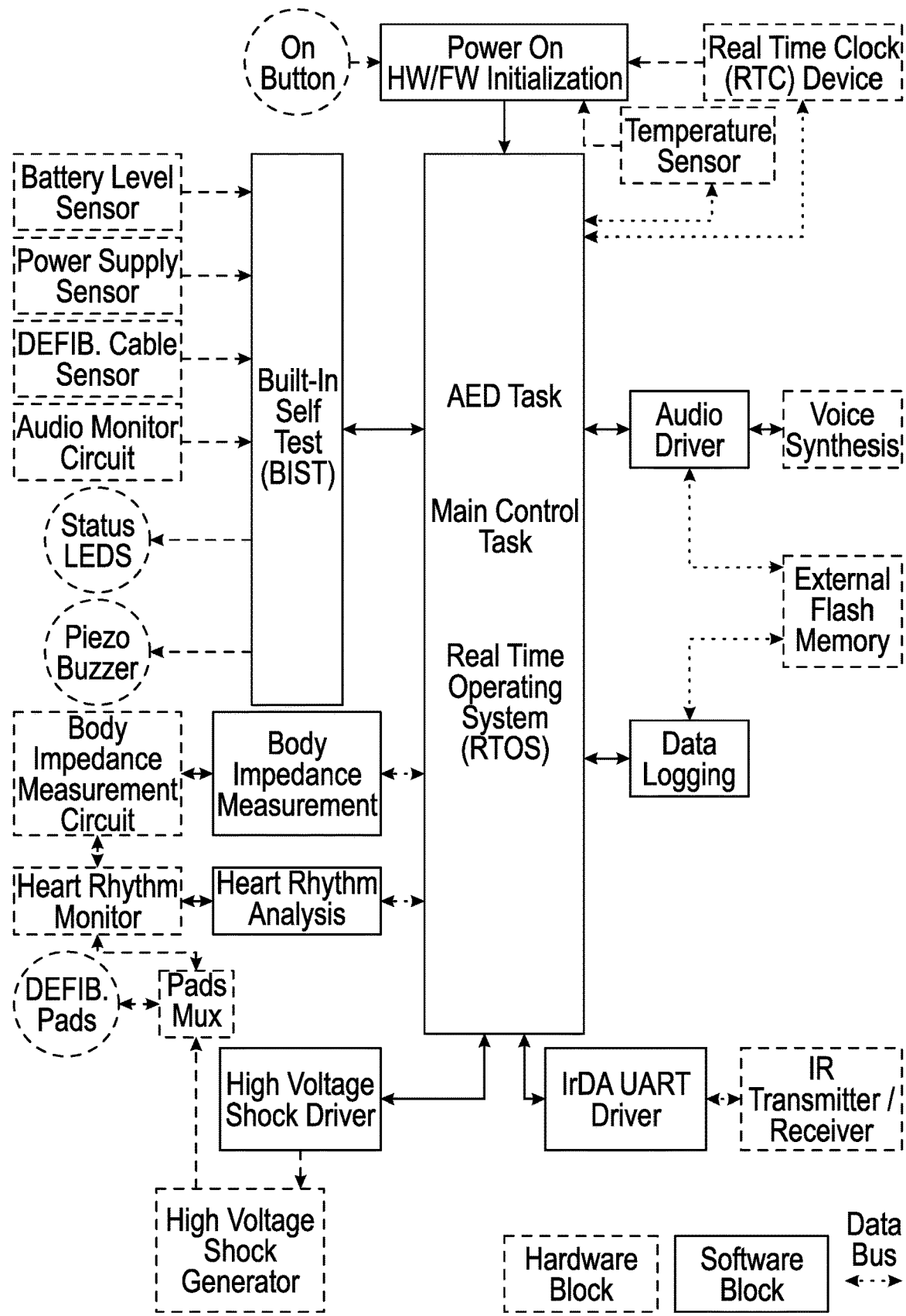
FIG. 5 is a software block diagram for an AED device, according to one embodiment of the disclosed invention.

FIG. 5 is a software block diagram depicting the arrangement and interaction of these electronic components. The functions of the AED device 100 may be classified into one of two categories: defibrillation tasks and Built-In Self-Test (BIST) tasks. While the defibrillation tasks can only be performed when the AED device 100 is fully powered on, the BIST tasks will be performed regardless of whether the AED device 100 is on or off.

In addition to these two primary task categories, the AED device 100 also utilizes an audio driver (not shown), which is responsible for interfacing between the voice synthesizer device and the SD card 320 where these audio files are stored. While defibrillation and BIST tasks are being performed, the audio driver draws the appropriate voice file from the SD card 320, routes the audio to the voice synthesizer, and plays the audio for the user.

The AED device 100 also utilizes a data logging task, which also forms an interface with the SD card 320. Any data collected during the defibrillation or BIST tasks is stored on the SD card 320, which can later be retrieved on an external device. The AED device 100 also includes an IrDA UART driver to interface with an IR transmitter or receiver. The IrDA UART functions to communicate with compatible devices. For example, the IrDA UART may transmit logged data, or receive firmware updates to be installed on the AED device 100.

Returning to the primary AED device 100 tasks, FIGS. 6-10 provide additional detail regarding the primary defibrillation tasks, which include charging the HV Cap 302, performing a Z-Body measurement, taking and analyzing the patient's ECG, and administering a shock. Because the defibrillation tasks require that the AED device 100 be fully powered on, the user must turn on the AED device 100 to initiate any of these tasks. To do so, the user depresses the ON button 106, which is connect to power button 308, which enables the microprocessor 602 to power up the internal assembly 300.

Figure 6:
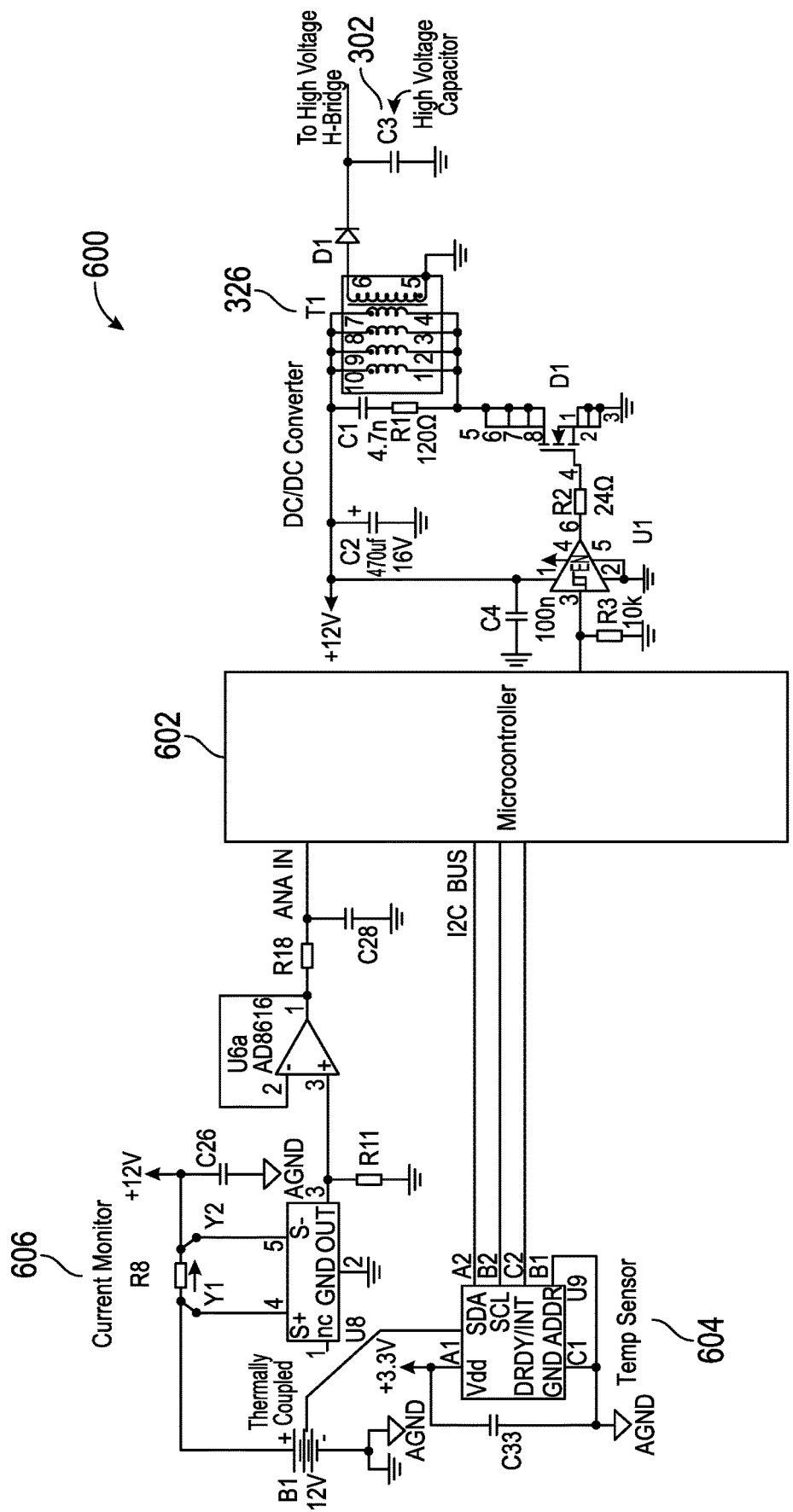
FIG. 6 is an example of a high voltage capacitor charging circuit, according to one embodiment of the disclosed invention.

FIG. 6 depicts an exemplary embodiment of the HV Cap 302 charging circuit 600. The AED device 100 uses a flyback topology DC/DC converter 600 depicted on the FIG. 6 to raise the battery voltage (approx. 12 volts) to a sufficiently high voltage for a shock pulse (up to 2000 volts).

The converter consists of the Field Effect Transistor (FET) switch 3002, driver 3003, snubber circuit 3006, transformer 326 and rectifying diode 3004. The microcontroller 602 generates trail of pulses, under software control, that get amplified by the driver 3003 in order to operate the gate of the FET switch 3002. The switch periodically opens and closes, allowing current to flow or interrupting the current through the primary winding of the transformer 326. When the current is interrupted, a back Electro-Magnetic Force (EMF) voltage is generated on the primary winding of the transformer 326, according to Lenz's Law describing this fundamental property of inductors.

Because of amount of turns of the secondary winding of the transformer 326 is much larger than the primary, the EMF voltage on the secondary winding gets multiplied by the turns ratio between primary and secondary windings. The ratio is chosen such that the peak of back EMF pulses can reach 2000 volts. This voltage is rectified by the diode 3004 which charges the HV cap 302.

In a preferred embodiment, the AED device 100 uses CR2 batteries to power the AED device 100 and charge the HV Cap 302. Because the batteries are significantly smaller than those used in conventional AED devices, the HV Cap 302 requires more time to charge than for the conventional AED devices. Conventional AED devices also typically do not begin charging until a shockable heart rhythm is detected. Therefore, to account for the smaller batteries, the AED device 100 begins charging the HV Cap 302 immediately after the AED device 100 is turned on and before seeking to detect whether a shockable heart rhythm exists. According to a preferred embodiment, the HV Cap 302 will be fully charged within 30-40 seconds of the AED device 100 being turned on.

The microprocessor 602 is programmed to monitor and control the charging rate of the HV Cap 302. To charge the HV Cap 302, the microprocessor 602 transmits a sequence of square wave pulses from the HV XFMR 326 to the HV Cap 302, where the frequency of these pulses effectively controls the HV Cap 302 charging rate. Thus, the microprocessor 602 is programmed with a feedback loop that will adjust the frequency of the pulses in order to adjust the charging rate as necessary.

In particular, the microprocessor 602 of the presently disclosed AED device is configured to modify the charging rate to ensure the batteries are not exceeding the manufacturer specified discharge rate and temperature, which is 1000 mA and 60° C. for CR2 batteries. The charging circuit 600 therefore includes a temperature sensor 604 and a current monitor 606 to collect and provide feedback to the microprocessor. This process ensures that the HV Cap 302 is charging at the fastest possible rate given the available battery power at the time.

Additionally, the microprocessor 602 of the presently disclosed AED device is configured to modify the charging rate to account for functions of the AED device 100 that occur while the HV Cap 302 is charging. For example, the speaker 310 will be giving the user various instructions during the charging process. To account for the current that the speaker 310 is drawing from the batteries, the microprocessor 602 will appropriately decrease the current to the HV Cap 302 to keep the batteries within the specified discharge and temperature thresholds. And when the voice prompt is complete, the microprocessor 602 will return to the original charging rate.

While the HV Cap 302 is charging, the AED device 100 performs two defibrillation tasks before a shock can be administered, the first of which is performing a body impedance (Z-Body) measurement. A Z-Body measurement incorporates both the resistance and capacitance of a patient's body when a AC current is applied. The Z-Body measurement is critical in determining the magnitude of the shock to be delivered. In particular, the shock administered by the AED device 100 is only effective if the magnitude of the current is high enough to depolarize the heart. But the current cannot be so high that it damages the patient's cardiac tissue. Thus, the Z-Body measurement ensures the shock is within this effective, non-damaging range.

Figure 7:
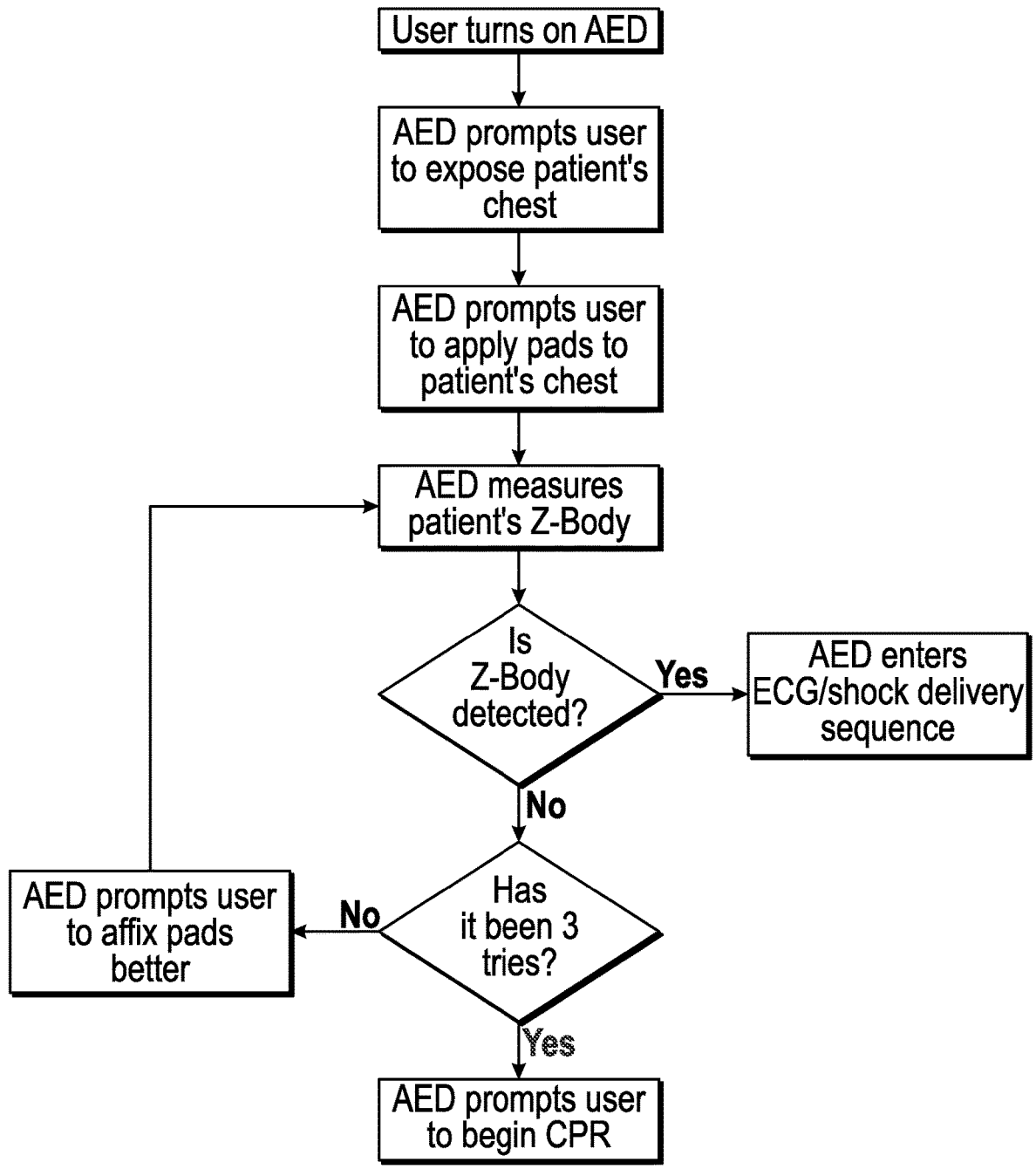
FIG. 7 is a block diagram depicting a Z-Body measurement sequence, according to one embodiment of the disclosed invention.
Figure 8:
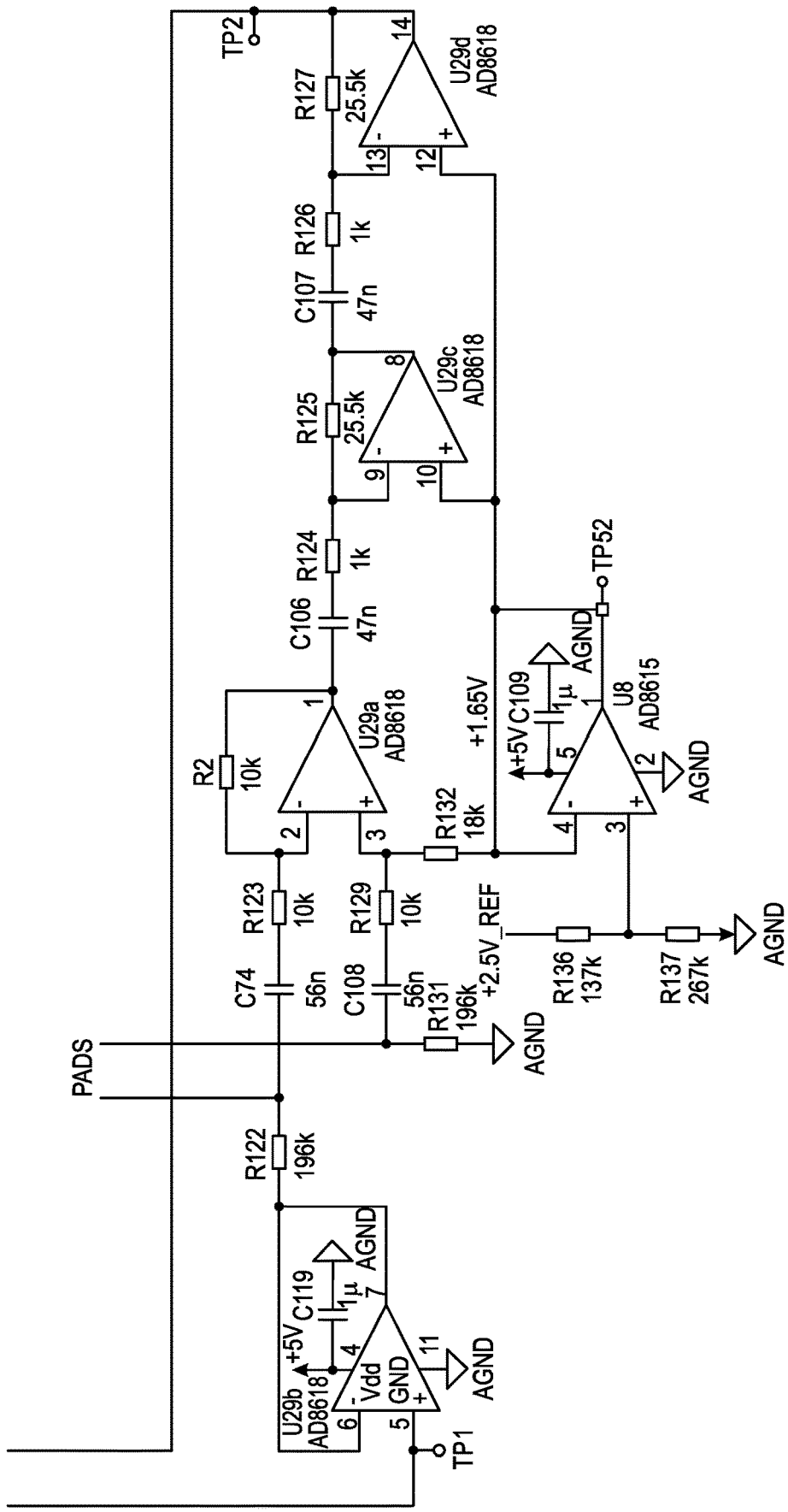
FIG. 8 is an example of a conventional Z-Body measurement circuit common in the prior art.
Figure 9:
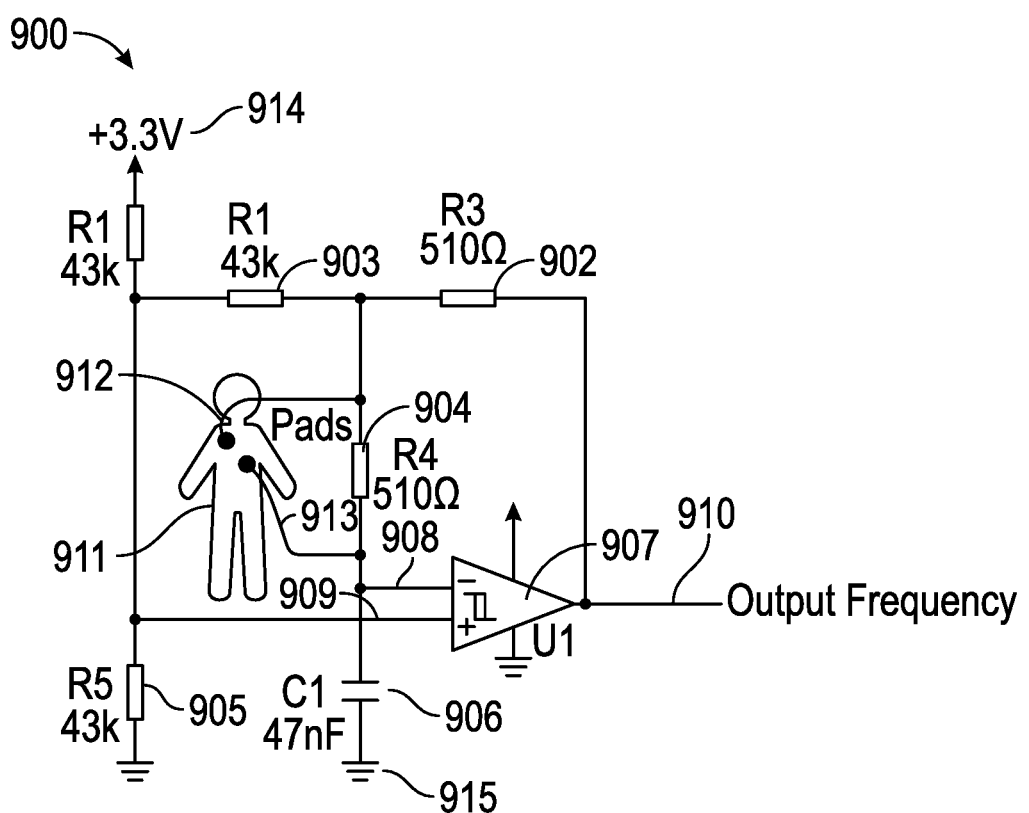
FIG. 9 is an example of a Z-Body measurement circuit utilizing a relaxation oscillator, according to one embodiment of the disclosed invention.

The process of performing a Z-Body measurement is shown in FIG. 7. After the user has turned on the AED device 100 and properly placed the defibrillator pads 202, 204 on the patient's chest, the AED device 100 will attempt to detect a Z-Body measurement. According to an exemplary embodiment, the AED device 100 performs the Z-Body measurement with a relaxation oscillator circuit 900, as shown in FIG. 9. This process is much different from conventional AED devices, which use circuits such as that of FIG. 8 to perform the Z-Body measurement. The conventional process of performing Z-Body measurements generally involves sending a constant, high frequency AC signal through the defibrillator cables and pads, which is subject to significant outside interference. Accordingly, conventional AED devices must use expensive precision circuit components to measure these signals and filter the inevitable interference.

It is therefore advantageous to use a relaxation oscillator circuit 900 because it is simpler in design (and is less expensive), takes up less space and has more immunity to interference than conventional Z-Body measurement circuits.

The circuit 900, shown in FIG. 9, self-oscillates at the frequency defined by its timing components. The basic idea behind using this type of oscillator for the Z-body measurement is to include the human body as one of the timing components for the oscillator and capturing the frequency changes it produces. After calibration, measurement of the output frequency of the circuit will determine the Z-body value of the only variable component (the human body) that caused the change.

In a preferred embodiment, the circuit includes a voltage comparator 907, integrated into microprocessor 602 having its inverting input 908, non-inverting input 909 and output 910, a voltage divider 901 and 905 and a timing RC circuit with fixed resistor 904 and capacitor 906. A human body 911, seen by the circuit as a resistor is connected in parallel to resistor 904 through two cables called Apex 912 and Sternum 913.

The feedback resistor 902 provides positive feedback required to start the oscillation process. Resistor 903 is used to scale the magnitude of the feedback signal. The circuit is powered from the power source 914 relative to the ground potential 915. The comparator 907 is an electronic device whose output state can have only two predefined values: approximately volts (V) or near the power supply voltage depending on the status of its inputs. In case of an AED supplying the circuit with 3.3V, the comparator's output 910 will be approximately 0V or 3.3V. The comparator 907 compares the voltages on its inputs 908, 909 and sets the output 910 accordingly. If the non-inverting input's 909 voltage is higher than inverting input's 908 voltage, then the output 910 will be set to 3.3V. Otherwise the output 910 is will be at 0V.

The operation of the circuit 900 is as follows:

Upon applying power 914, the voltage on the non-inverting input 909 of the comparator 907 is set according to voltage divider 901 and 905, padded by the Apex 912 voltage through the calibration resistor 903. With resistors 901 and 905 set to equal values, it will be half of the supply voltage 914, or 1.65V, in this example. However, it will be increased or reduced depending on the voltage on the Apex 912 wire applied to the input 909 through resistor 903, which, in turn, depends on the status of the comparator's output 910. Based on the chosen values of the components, the non-inverting input 909 voltage will be about 1.55V when output 910 is 0V and 1.75V when output 910 is at 3.3V.

Initially the voltage on the inverting input 908 will be near zero because the capacitor 906 is initially discharged, therefore output 910 of the comparator 907 will be set to 3.3V. This voltage is applied to the capacitor 906 through the feedback resistor 902 and timing resistor 904 in parallel to human body 911 impedance (Z-Body). The capacitor 906 will start charging from the current flowing through the resistor 904 and the human body 911 up towards the voltage set by the voltage divider formed by feedback resistor 902 and calibrating resistor 903. The divider ratio is set so that final voltage on Apex wire 912 will be higher than 1.75V.

When the voltage on the capacitor 906 connected to inverting input 908 exceeds 1.75V which is present on the non-inverting input 909, comparator's 907 output 910 flips from 3.3V to 0V. This causes Apex 912 voltage to decrease to a value below 1.55V which immediately changes the voltage on non-inverting input 909 to 1.55V.

The capacitor 906 then starts discharging through resistor 904 and the human body 911. When it discharges from 1.75V to 1.55V, the non-inverting input's voltage becomes higher than inverting input's voltage, and the cycle repeats, generating a digital frequency (between 0V and 3.3V) on the comparator's 907 output 910.

As mentioned above, the time required for the capacitor 906 to keep charging from 1.55V to 1.75V and discharging back from 1.75V to 1.55V depends on the RC constant where R consists of resistor 904 and human body 911 impedance (Z-Body) in parallel. Because resistor 904 is constant and known, the only variable determining final oscillation period (e.g., frequency) on the comparator's 907 output 910 is the human body 911 impedance (Z-body). By calibrating the oscillator against a known set of impedances, the human body's 911 contribution to the oscillator's frequency change can be determined from frequency of the signal on the comparator's 907 output 910 and computing Z-Body value.

Accordingly, the microprocessor 602 requires fewer variables to compute the Z-Body measurement. Moreover, the relaxation oscillator circuit 900 is optimal as compared to conventional Z-Body measurement circuitry because it is entirely immune to outside interference because the relaxation oscillator 900 does not use and measure analog signals. And, as previously mentioned, the simplicity of the relaxation oscillator circuitry reduces the cost of manufacturing the device, as well as the size of the device, because fewer components are required.

Furthermore, the relaxation oscillator circuit 900 does not require the use of expensive, precision resistors or capacitors. The circuit uses a voltage comparator and only a few non-precision passive resistors and capacitors to drive the output signal, resulting in a greatly reduced component count over prior art Z-Body measurement circuits. A measurement of the output frequency of the circuit is used to determine the patient's body impedance. The output is a digital signal which allows the frequency to be measured independently of amplitude which yields greater noise immunity over prior art Z-Body measurement methods.

However, it is possible that in some circumstances the AED device 100 will not be able to take this measurement. Commonly, the AED device 100 will not take a Z-Body measurement if the defibrillator pads 202, 204 are not properly placed on the patient's chest. Accordingly, after a failed Z-Body measurement the user will be prompted to adjust the defibrillator pads 202, 204. In the event of three failed measurements, the user will be prompted to administer cardiopulmonary resuscitation (CPR) instead.

Figure 10:
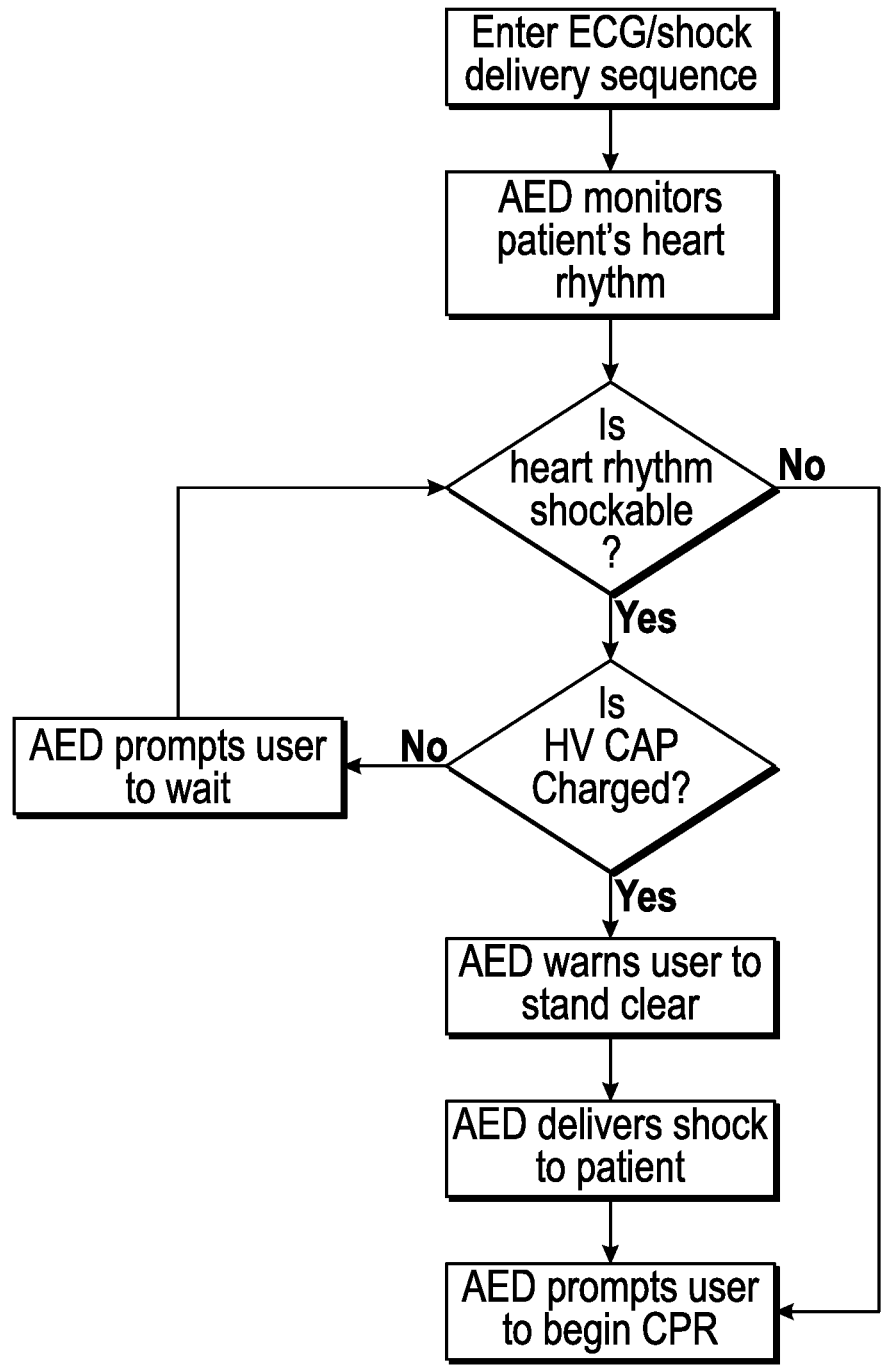
FIG. 10 is a block diagram depicting an ECG and shock delivery sequence, according to one embodiment of the disclosed invention.

If the AED device 100 is successful in performing the Z-Body measurement, the AED device 100 will proceed to the second defibrillation task, which involves reading and analyzing the patient's ECG. This process, which is generally shown in FIG. 10, monitors the patient's heart rhythm to determine whether the patient has one of two shockable rhythm patterns. Defibrillation is only effective when a patient is in ventricular tachycardia (Vtach) or ventricular fibrillation (Vfib), so the AED device 100 will prompt the user to administer CPR if neither of these two shockable rhythms are detected. If Vtach or Vfib is detected, and the HV Cap 302 is sufficiently charged, the AED device 100 will prompt the user to stand clear before administering the shock. Thereafter, the user will be prompted to administer CPR.

The process of detecting the patient's heart rhythms utilizes an Analog Front End (AFE) circuit (not shown) that is integrated into the main PCB 306. According to an exemplary embodiment, the AFE includes a MAX30003 integrated circuit (IC) (not shown) to not only capture the ECG data, but also control the gain, sample rate, bias, polarity, and filter adjustments necessary to maximize readability of the ECG signals. In this embodiment, the IC receives the patient's low voltage heart rhythms, which are transmitted to an analog-to-digital converter (ADC) (not shown). These digital outputs are sampled periodically, at which point the buffered data is transmitted to the microprocessor 602, which is programmed to determine whether the patient has a shockable heart rhythm. The AED device 100 must capture at least six (6) consecutive heart rhythms of a shockable pattern, or else a shock will not be delivered.

According to an exemplary embodiment, the AED device 100 utilizes a software high voltage (HV) shock driver (not shown) to interface between all the circuits involved in the defibrillation process. More specifically, the HV shock driver software measures the voltage of the HV Cap 302 after the Z-Body measurement is performed, to ensure the HV Cap 302 voltage is charged to an appropriate level. Moreover, the HV shock driver software also is responsible for controlling whether a shock is actually administered after ECG data is collected.

When the AED device 100 is powered up and the defibrillator pads 202, 204 are attached to the patient, the AED device 100 continuously measures the ECG waveform of the patient and classifies it in real time. When the classification is determined to be a shockable waveform, i.e. either (i) ventricular tachycardia (Vtach), or (ii) ventricular fibrillation (Vfib), and this classification remains constant for a minimum of six seconds of time, then a high voltage shock is delivered to the patient through the defibrillator pads.

To deliver a shock, the AED device 100 utilizes the H-Bridge circuitry 324 which transforms the energy released from the HV Cap into a bi-phasic pulse, which is defined as two pulses of opposite polarity applied in sequence. After the shock is delivered, the AED device 100 will prompt the user to administer CPR while continuing to monitor the patient's ECG. After two minutes of CPR, should the analysis of the patient's ECG determine that a second shock is needed, the above process will be repeated, and again, if necessary, for a third shock. In each case, the device will prompt the user to administer two minutes of CPR in between shocks.

In preferred embodiments, the AED device has no OFF button, in order to prevent the device from accidentally powering down at an inopportune moment. Instead, the device is configured to power off after a specified period of inactivity, e.g., after three minutes of total inactivity. The speaker 310 will alert the user that the AED device 100 is turning off.

Figure 11:
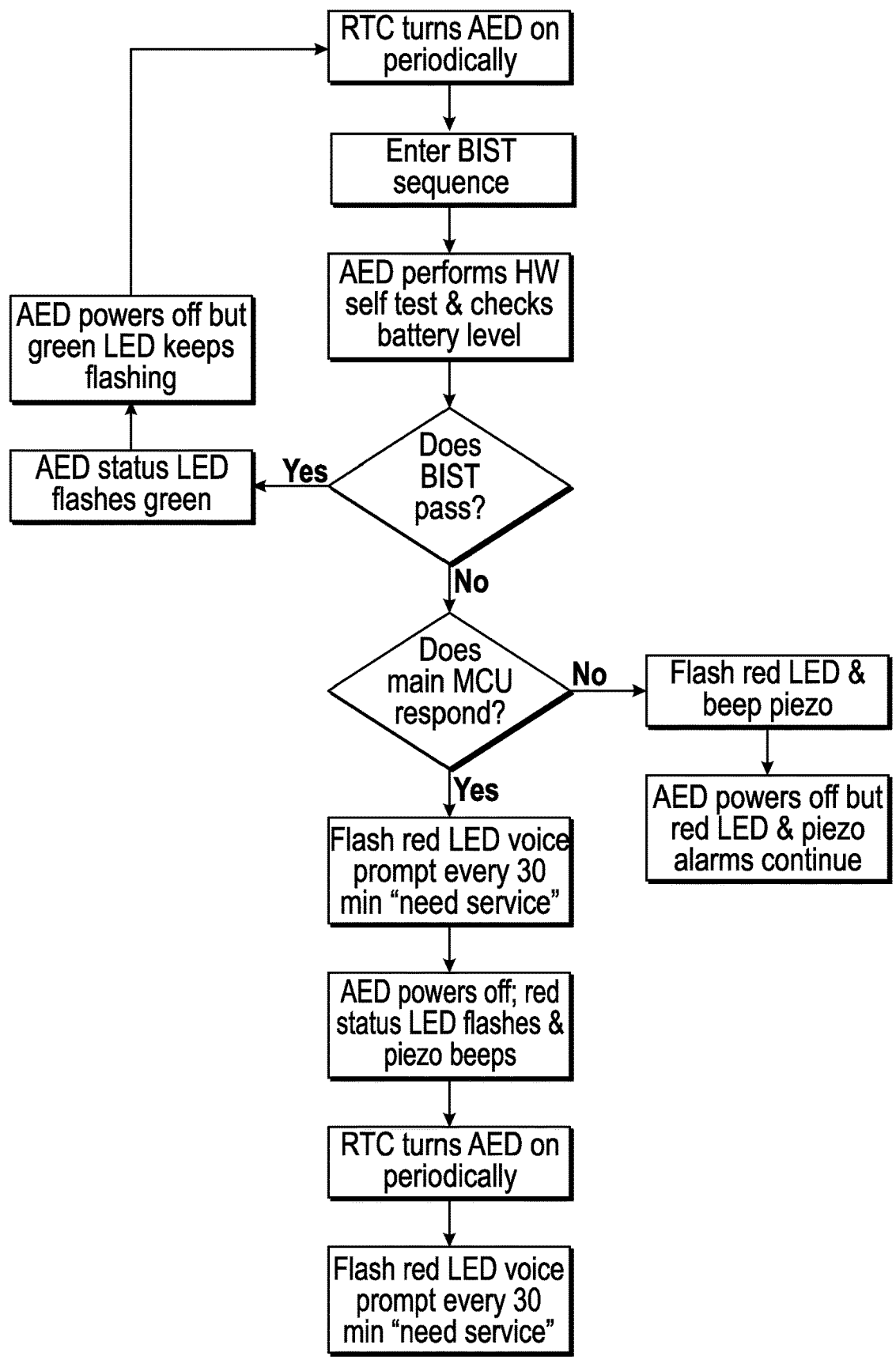
FIG. 11 is a block diagram depicting a Built-In Self-Test (BIST) sequence, according to one embodiment of the disclosed invention.

Aside from the previously described defibrillation tasks, the AED device 100 performs several Built-In Self-Test (BIST) tasks, in part according to the diagram of FIG. 11. In general, the BIST tasks ensure the AED device 100 is operating properly, and a majority of these BIST tasks are performed while the AED device 100 is off.

Because the present AED device uses significantly smaller batteries than conventional AED devices, the internal components are configured and programmed in such a way as to preserve as much battery power as possible. Accordingly, an exemplary embodiment of the AED device 100 includes a Power Handler system (not shown) to control the BIST tasks while preserving as much battery power as possible. More specifically, the Power Handler system ensures that all circuits, except for a few ultra-low power components, are off when the AED device 100 is not in use. The ultra-low power components that remain on at all times operate in the nanoamp range and include but are not limited to the Real Time Clock (RTC) (not shown). This Power Handler system is unique as compared to conventional AED devices, which often enter a "Sleep Mode" when not in use. However, sleep modes still consume large amounts of energy, making the present Power Handler system especially advantageous for reducing power consumed during long periods of inactivity.

In general, the RTC is programmed to periodically wake up the microprocessor 602 to initiate the BIST sequence, which involves a series of hardware verifications and a battery level check. When the BIST is successful—when no errors are identified—the AED device 100 status will be updated so that a green status LED 314 flashes periodically. This green status LED 314 will continue flashing after the microprocessor 602 turns off, until the next BIST sequence. If the BIST is not successful, and the speaker 310 is functioning properly, a red status LED 314 flashes as a voice prompt such as "Need Service" is administered. The microprocessor 602 will then turn off, and while doing so will flash the red status LED 314 and with a piezo buzzer 312 beep. This process is repeated every thirty minutes until the AED device 100 is serviced. When the speaker 310 is not functioning properly, or the microprocessor 602 is unresponsive, a red status LED 314 flashes while the piezo buzzer 312 beeps. These alarms are continuous, or continual, until the AED device 100 is serviced.

Figure 12:
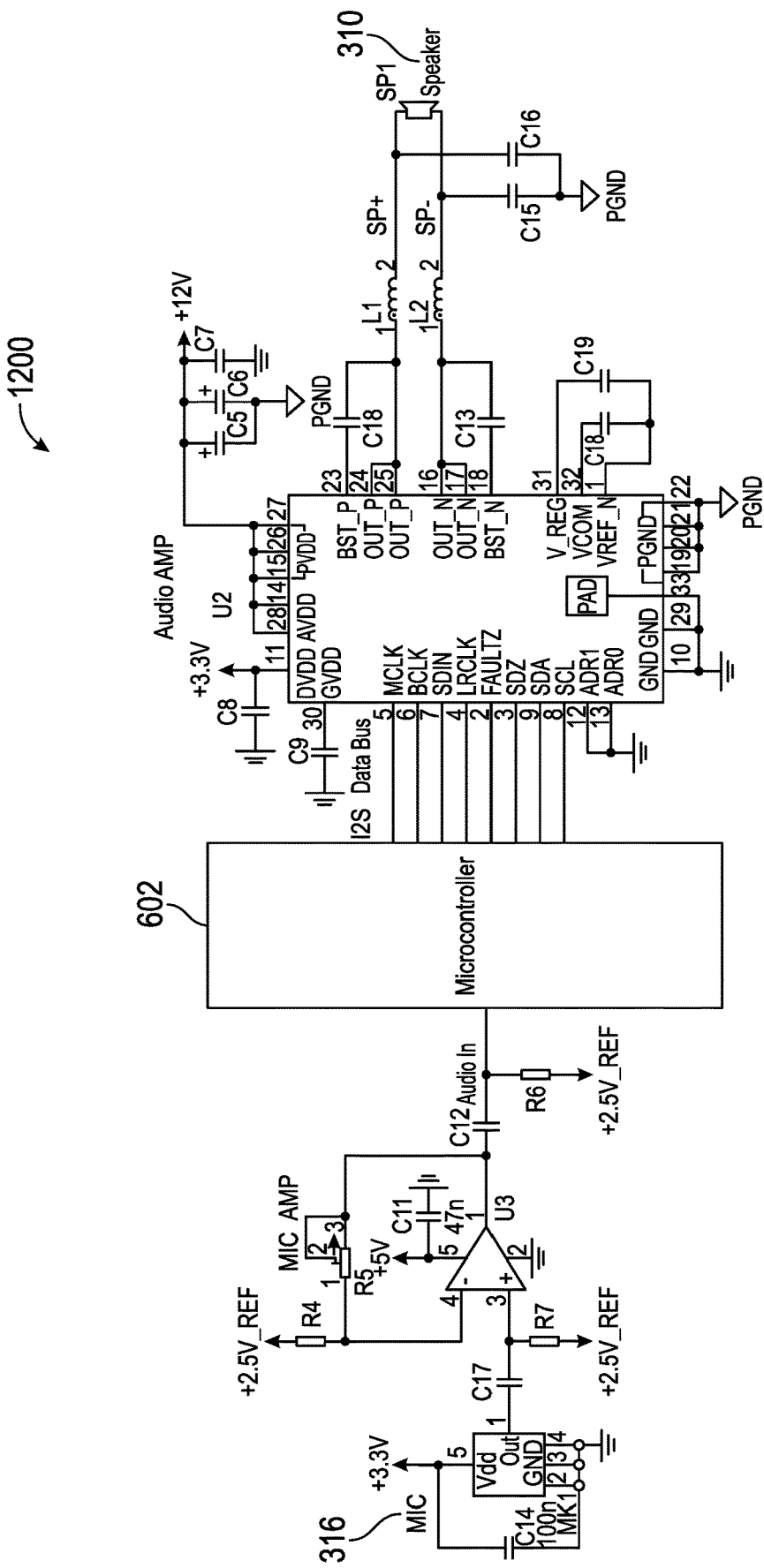
FIG. 12 is an example of a speaker verification circuit, utilizing microphone monitoring, according to one embodiment of the disclosed invention.

Turning to specific verifications performed during the BIST sequence, FIG. 12 depicts an exemplary speaker verification circuit 1200. The reliability, sound pressure level, and integrity of the voice prompts are important in guiding the user's use of the AED device, so the speaker 310 should be frequently monitored. According to an exemplary embodiment, the speaker 310 is integrated into the housing using an O-ring or gasket (not shown) to achieve splash-proofing or waterproofing to an acceptable ingress protection (IP) level. The speaker holes 110 in the housing 102 allow sound pressure from the speaker 310 to exit the AED device 100, but render the speaker potentially susceptible to damage, e.g., by water or a sharp object penetrating the speaker holes. Damage of this sort may be imperceptible to the naked eye but may cause voice prompts to be distorted or even nonexistent.

According to an exemplary embodiment, the main PCB 306 is fitted with a small microphone 316 positioned in close proximity to the speaker 310. When powered up by the RTC, the microprocessor 602 generates a brief tone lasting approximately 20-50 msec, which plays through the speaker 310. The microprocessor 602 also "listens" for this tone to be repeated through the microphone 316. If the speaker 310 is damaged in any way, the tones will not match and the microprocessor 602 will enter the necessary alert sequence, as previously described.

Another potential vulnerability for a portable AED device is the temperature of the device. More specifically, an AED device is susceptible to damage when stored in high temperature environments that exceed the AED device's specified operating and storage temperature ranges. According to an exemplary embodiment, the AED device 100 utilizes a temperature sensor integrated circuit (temp-sense IC), generally shown in FIG. 6, to monitor the temperature of the AED device 100 at all times. The temp-sense IC, like the RTC, is an ultralow power component, and therefore will monitor the temperature of the AED device even when the microprocessor 602 is off. When the temperature of the AED device 100 falls outside the acceptable range, the temp-sensor IC powers up the microprocessor 602, which will enter the necessary alert sequence.

The present AED device is also uniquely vulnerable to damage to the defibrillator cables 104 and defibrillator pads 202, 204. Conventional AED devices are typically stored in secure, wall-mounted casings so the individual components are not likely to be damaged by ordinary acts of passersby. In contrast, because the presently disclosed AED device is intended for personal use, the AED device may be susceptible to tampering and damage in ways conventional AED devices are not, e.g., while being left in home and/or carried in vehicles and outdoors, whereby the AED device may be dropped, or exposed to water and varying temperatures, etc. To ensure that the defibrillator pads 202, 204 and defibrillator cables 104 are in working order, the AED device 100 has several methods for verifying the pad 202, 204 and cable 104 integrity.

According to a first exemplary embodiment, during the BIST sequence the microprocessor 602 generates a low frequency signal, approximately 30 kHz, and sends this signal through the defibrillator cables 104 and defibrillator pads 202, 204. If the signal returns to the microprocessor 602 and matches the original, within a predetermined margin of error, the defibrillator cables 104 and defibrillator pads 202, 204 are intact. When there is a significant change in the signal, it is likely that the defibrillator pads 202, 204 are no longer properly sealed, or that the conductive gel layer 203, 205 has dried out. If no signal is returned at all, at least one of the defibrillator pads 202, 204 and/or defibrillator cables 104 is significantly damaged. In either case where the sent and returned signals do not match, the microprocessor 602 will initiate the necessary alert sequence.

In another exemplary embodiment, the pressure-sensitive laminated paper 206 between the positioned between the defibrillator pads 202, 204 has at least one small hole so that the conductive gel layers 203, 205 are in direct contact. Here, the microprocessor 602 is programmed to periodically generate a low voltage DC signal, approximately 3-5 VDC, that is sent through the defibrillator cables 104 and defibrillator pads 202, 204. As with the previously described embodiment, the microprocessor 602 compares the returned signal—in the event that a signal is returned—to the original signal to determine whether the defibrillator cables 104 or defibrillator pads 202, 204 is damaged. The microprocessor 602 will initiate the proper alert sequence as necessary when damage to at least one of the defibrillator pads 202, 204 and/or defibrillator cables 104 is detected.

According to yet another embodiment, the integrity of the defibrillator cables 104 and defibrillator pads 202, 204 is verified using a method similar to that described with respect to performing the Z-Body measurement. In particular, this verification method utilizes the relaxation oscillator circuit of FIG. 9. During the BIST sequence, the relaxation oscillator will initiate an oscillation within an established frequency range. The microprocessor 602 detects this oscillation and thereafter calculates the oscillation frequency. When the calculated oscillation frequency is within the established range, the defibrillator cables 104 and defibrillator cables 202, 204 are functioning properly. If the calculated frequency is outside this range, or the microprocessor 602 cannot detect the oscillation, at least one defibrillator pad 202, 204 and/or defibrillator cable 104 is damaged and the microprocessor 602 will enter the necessary alert sequence.

The FDA requires that defibrillator pads of AED devices are changed at least every two years. Thus, according to an exemplary embodiment, the RTC is programmed with a timer that will alert the microprocessor 602 every two years when the defibrillator pads 202, 204 must be changed. When the microprocessor 602 is alerted that service is required, it will initiate a predetermined alert sequence to inform the user that new defibrillator pads 202, 204 are needed.

Figure 13:
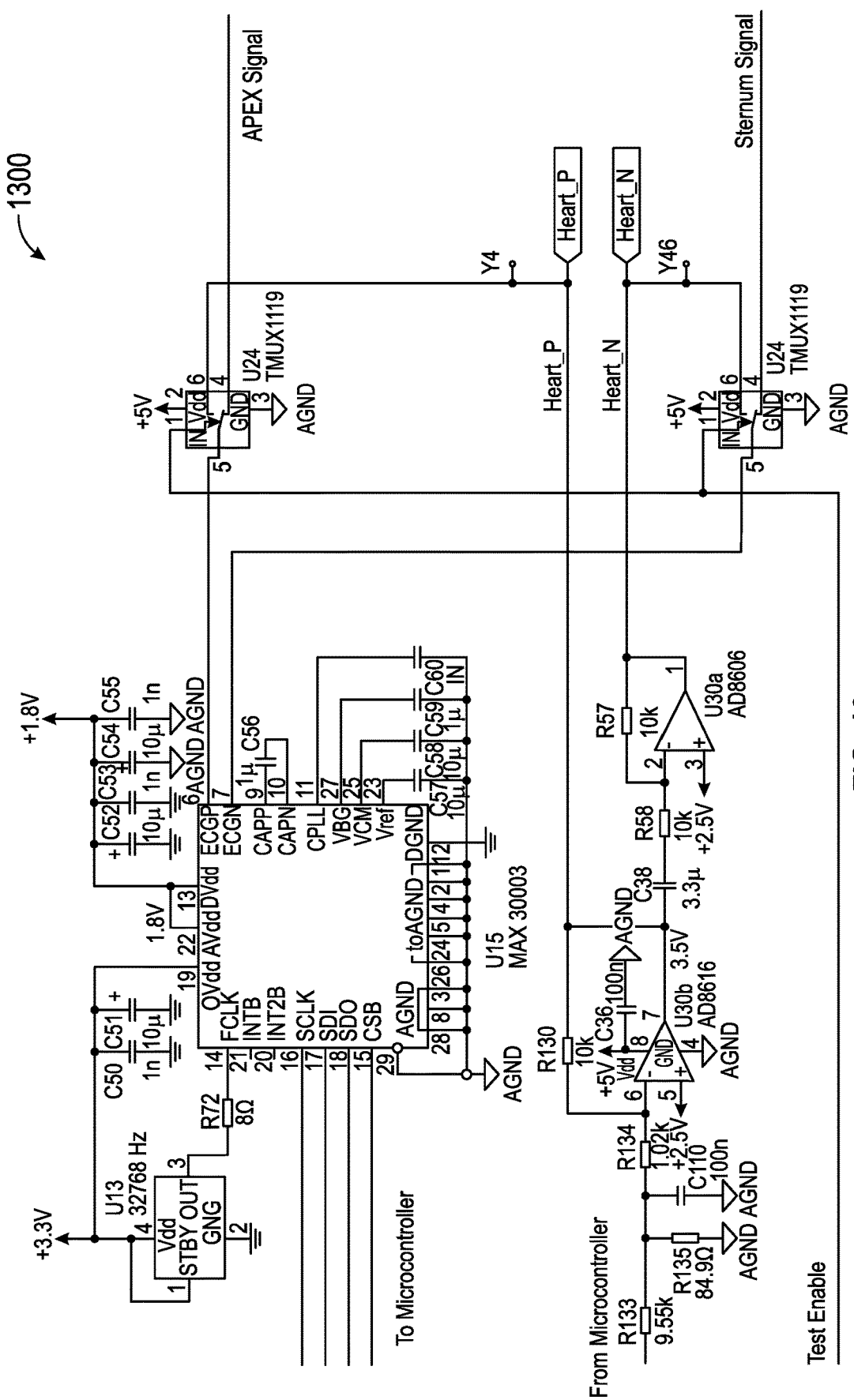
FIG. 13 is an example of an analog front end verification circuit, according to one embodiment of the disclosed invention.

The BIST sequence also involves verifying the functionality of the AFE circuit. According to an exemplary embodiment, this process is executed using the circuit depicted in FIG. 13. When the AED device 100 enters the BIST sequence, the microprocessor 602 transmits a low-frequency signal that simulates a heartbeat, approximately 1-5 Hz, to the AFE circuit. If this signal is received, the AFE circuit reads and processes the signal as if it is collecting ECG data and will process and report the data to the microprocessor 602 accordingly. The AFE circuit is considered to be functioning properly when the data returned to the microprocessor 602 matches the original signal, within a predetermined margin of error. However, if no data is returned, or if the data returned falls outside of the predetermined margin of error, the microprocessor 602 will enter the necessary alert sequence.

Moreover, the BIST sequence involves several additional verifications. According to an exemplary embodiment, the BIST sequence also verifies the power supply voltage and battery status. When the power supply voltage is low, or there is an error detected in the battery status, the user will be properly alerted. However, the AED device 100 is equipped with a backup battery 318 to ensure that components such as the RTC, are always powered. The backup battery 318 is also critical to power the AED device 100 while the batteries are being serviced (e.g., replaced).

The BIST sequence also verifies the RAM and SD card 320 functionality. A primary purpose of the SD card 320 is to retain information pertaining to the status of the AED device 100 and any particular components that are in need of service. According to an exemplary embodiment, the SD card 320 is easily removable and will upload all of the status information for the AED device 100 to a computer. This upload enables the user to easily identify whether the AED device 100 needs service, and if so, identify what component and/or system requires service.

Further, according to another exemplary embodiment, the microphone 316 may also record the audio of the ambient environment while the device is in use. Accordingly, the AED device 100 or, more specifically, the SD card, must have enough storage to retain this audio data. This data may be used to provide forensic information for any failed revival attempts.

The BIST sequence also implicitly verifies the functionality of the microprocessor 602. More specifically, the microprocessor 602 is not functioning properly if, during any of the aforementioned tasks, the microprocessor 602 is unresponsive. In such an instance, the secondary microprocessor takes over a limited number of the processing functions. In particular, the secondary microprocessor will initiate the appropriate alert sequence to inform the user service is required.

As used herein, the term "about" means plus or minus 10% of the numerical value of the number with which it is being used.

While the disclosure has been described with reference to a number of exemplary embodiments, it will be understood by those skilled in the art that the disclosure is not limited to such disclosed embodiments. Rather, the disclosed embodiments can be modified to incorporate any number of variations, alterations, substitutions, or equivalent arrangements not described herein, but which are within the scope of the disclosure.

That which is claimed is:

1. An Automated External Defibrillator (AED) device comprising:
   a high voltage capacitor (HV Cap) configured to store the energy required to deliver a defibrillation shock to a patient;
   one or more batteries configured to charge the HV Cap;
   a DC/DC converter circuit comprising a high voltage transformer (HV XFMR), a field effect transistor (FET) switch with associated driver, and a rectifying diode;
   an H-bridge circuit configured to transform energy released from the HV Cap into a bi-phasic pulse; and
   a memory and a microprocessor which are configured to store and execute computer-executable instructions for operation of the AED device,
   wherein the HV Cap, the DC/DC converter circuit, the H-bridge circuit, the one or more batteries, and the memory and the microprocessor are contained in a pocket-sized housing, and
   wherein the microprocessor is configured to monitor and adjust the charge rate of the HV Cap so as not to exceed (i) a maximum discharge rate of the one or more batteries, and (ii) a maximum operating temperature of the one or more batteries, thereby enabling the HV Cap to be charged at the maximum rate possible with available battery power.

2. The AED of claim 1, wherein the DC/DC converter circuit is configured to increase the battery voltage to about 2000 volts.

3. The AED of claim 1, further comprising:
   a pair of defibrillator pads, and
   a cable for operably connecting the HV Cap to the pair of defibrillator pads, wherein the defibrillator pads are pocket-sized.

4. The AED device of claim 1, wherein the housing has dimensions that are 155 mm×86 mm×28 mm or smaller.

5. The AED device of claim 1, wherein the one or more batteries consist of four CR2 batteries.

6. The AED device of claim 1, wherein the HV Cap is configured to begin charging when the AED device is powered on.

7. The AED device of claim 1, wherein the maximum battery discharge rate is 1000 mA and the maximum operating temperature is 75° C.

8. The AED device of claim 1, further comprising a real time clock (RTC) and a temperature sensor integrated circuit (Temp Sensor IC), each of which is configured to power up the AED device according to dynamic parameters programmed into the RTC and Temp Sensor IC, wherein the microprocessor is configured to be powered completely off (not in sleep mode) when the AED device is not in use.

9. The AED device of claim 8, wherein, when the AED device is not in use, all circuits and components are powered off with the exception of the RTC, the Temp Sensor IC, and their supporting circuitry.

10. The AED device of claim 8, wherein the RTC is configured to periodically power up the microprocessor to perform a series of Built-In Self Tests (BIST) to check the one or more batteries, circuitry, and other hardware of the AED device.

11. The AED device of claim 8, wherein the Temp Sensor IC is configured to continuously monitor the temperature of the AED device, including when the rest of circuitry of the AED device is powered down.

12. The AED device of claim 1, further comprising:
a speaker contained in the housing and configured to provide voice prompts to a user; and
a microphone disposed in the housing near the speaker and the RTC is configured to periodically power up the microprocessor to perform a BIST in which a signal is sent from the microprocessor through the speaker, and the microprocessor compares the sent signal with the signal received through the microphone to assess the integrity of the speaker.

13. The AED device of claim 12, wherein, during use, AED device is configured to record, and has an external flash memory to store, audio received by the microphone during the operation of the AED device.

14. The AED device of claim 1, further comprising a low power microcontroller which is configured (i) to be powered on periodically by a signal from the RTC and monitor the temperature of the AED device housing and/or the defibrillator pads, and (ii) to power on and alert the microprocessor if the monitored temperature has reached a specified temperature.

15. The AED device of claim 1, which comprises a variable frequency relaxation oscillator circuit configured for use in a Z-body measurement, wherein the circuit is effective to self-oscillate at a frequency that is proportional to the patient's body impedance.

16. The AED device of claim 1, wherein the microprocessor is configured to verify the integrity of the defibrillator pads and cables.

17. The AED device of claim 1, wherein the microprocessor is configured to verify the integrity of electrocardiogram (ECG) circuitry in the AED device.

18. The AED device of claim 17, wherein the microprocessor is configured to periodically generate a signal that simulates a heartbeat and send the signal to Analog Front End (AFE) circuitry and then to compare the sent signal with a signal that has been processed by the AFE circuitry.

19. An Automated External Defibrillator (AED) device comprising:
a high voltage capacitor (HV Cap) configured to store the energy required to deliver a defibrillation shock to a patient;
one or more batteries configured to charge the HV Cap;
a DC/DC converter circuit comprising a high voltage transformer (HV XFMR), a field effect transistor (FET) switch with associated driver, and a rectifying diode;
an H-bridge circuit configured to transform energy released from the HV Cap into a bi-phasic pulse;
memory configured to store computer-executable instructions; and
at least one microprocessor configured to access the memory and execute the computer-executable instructions to continuously monitor and adjust the rate at which the one or more batteries charge the HV Cap,
wherein the AED device is configured to simultaneously monitor discharge current and temperature of the one or more batteries in order to charge the HV Cap at the maximum rate possible with available power from the one or more batteries, while not exceeding either a maximum temperature or a maximum discharge rate of the one or more batteries.

20. The AED device of claim 19, wherein:
the one or more batteries consist of four CR2 batteries; and
the HV Cap, the DC/DC converter circuit, the H-bridge circuit, the one or more batteries, the memory, and the microprocessor are contained in a pocket-sized housing.

* * * * *